(12) United States Patent
Shah et al.

(10) Patent No.: US 11,291,286 B2
(45) Date of Patent: *Apr. 5, 2022

(54) COSMETIC COMPOSITIONS WITH A MICRO-MESH STRUCTURE

(71) Applicant: ELC Management LLC, Melville, NY (US)

(72) Inventors: Snehal Shah, Nesconset, NY (US); Hua Wang, Islip, NY (US); Zhequan Xu, Shanghai (CN); Mary Ann Smail, Commack, NY (US); Milan Franz Sojka, Coram, NY (US); Daniela Bratescu, Northport, NY (US)

(73) Assignee: ELC MANAGEMENT LLC, Melville, NY (US)

( * ) Notice: Subject to any disclaimer, the term of this patent is extended or adjusted under 35 U.S.C. 154(b) by 63 days.

This patent is subject to a terminal disclaimer.

(21) Appl. No.: 16/851,077

(22) Filed: Apr. 16, 2020

(65) Prior Publication Data

US 2020/0329844 A1    Oct. 22, 2020

Related U.S. Application Data

(63) Continuation of application No. 15/832,493, filed on Dec. 5, 2017, now Pat. No. 10,660,420.

(60) Provisional application No. 62/434,717, filed on Dec. 15, 2016.

(51) Int. Cl.
| | |
|---|---|
| A45D 34/04 | (2006.01) |
| A45D 40/26 | (2006.01) |
| A61Q 19/00 | (2006.01) |
| A61K 8/02 | (2006.01) |
| A61Q 1/02 | (2006.01) |
| A61Q 19/08 | (2006.01) |
| A61K 8/73 | (2006.01) |
| A61K 8/81 | (2006.01) |
| A61K 8/87 | (2006.01) |
| A61K 8/88 | (2006.01) |

(52) U.S. Cl.
CPC ........... *A45D 34/04* (2013.01); *A45D 34/045* (2013.01); *A45D 34/046* (2013.01); *A45D 40/262* (2013.01); *A45D 40/265* (2013.01); *A45D 40/267* (2013.01); *A61K 8/0204* (2013.01); *A61K 8/025* (2013.01); *A61K 8/0208* (2013.01); *A61K 8/0212* (2013.01); *A61K 8/731* (2013.01); *A61K 8/733* (2013.01); *A61K 8/735* (2013.01); *A61K 8/8129* (2013.01); *A61K 8/8147* (2013.01); *A61K 8/8152* (2013.01); *A61K 8/87* (2013.01); *A61K 8/88* (2013.01); *A61Q 1/02* (2013.01); *A61Q 19/00* (2013.01); *A61Q 19/005* (2013.01); *A61Q 19/08* (2013.01); *A61K 2800/412* (2013.01); *A61K 2800/87* (2013.01)

(58) Field of Classification Search
CPC ....... A61K 8/8152; A61K 8/735; A61K 8/733
See application file for complete search history.

(56) References Cited

U.S. PATENT DOCUMENTS

| | | | |
|---|---|---|---|
| 2,173,959 A | 9/1939 | Britt | |
| 2,623,229 A | 12/1952 | Curt | |
| 2,681,463 A | 6/1954 | Gordon | |
| 3,439,088 A | 4/1969 | Edman | |
| 3,818,105 A | 6/1974 | Coopersmith et al. | |
| 3,867,352 A | 2/1975 | Akamatsu et al. | |
| 4,124,720 A * | 11/1978 | Wenmaekers | A61K 8/733 |
| | | | 514/452 |
| 4,960,339 A | 10/1990 | Iizuka et al. | |
| 5,077,211 A | 12/1991 | Yarosh | |
| 5,190,389 A | 3/1993 | Vasas | |
| 5,190,762 A | 3/1993 | Yarosh | |
| 5,272,079 A | 12/1993 | Yarosh | |
| 5,296,231 A | 3/1994 | Yarosh | |
| 5,324,128 A | 6/1994 | Gueret | |
| 5,346,935 A | 9/1994 | Suzuki et al. | |
| 5,599,125 A | 2/1997 | Vasas et al. | |
| 5,816,728 A | 10/1998 | Nardolillo et al. | |
| 6,010,265 A | 1/2000 | Bouix | |
| 6,076,985 A | 6/2000 | Gueret | |
| 6,168,334 B1 | 1/2001 | Fordham | |
| 6,197,319 B1 | 3/2001 | Wang et al. | |
| 6,270,273 B1 | 8/2001 | Ohba | |
| 6,298,864 B1 | 10/2001 | Gueret | |
| 6,375,374 B2 | 4/2002 | Gueret | |
| 6,685,963 B1 | 2/2004 | Taupin et al. | |
| 7,182,535 B2 | 2/2007 | Lim et al. | |

(Continued)

FOREIGN PATENT DOCUMENTS

| | | |
|---|---|---|
| CH | 705713 | 5/2013 |
| CN | 102973425 | 3/2013 |

(Continued)

OTHER PUBLICATIONS

JP-2001097888-A (Google English Translation, downloaded on Aug. 2021) (Year: 2021).*

(Continued)

*Primary Examiner* — Mark V Stevens
(74) *Attorney, Agent, or Firm* — Yonggang Wu

(57) ABSTRACT

A topical composition comprising a Polymer, a high molecular weight hyaluronic acid (HWM HA) and/or its salt, a low molecular weight hyaluronic acid (LWM HA) and/or its salt, and a polyamino acid and/or its salt; and water and a method for identifying a test polymer that forms a micro-mesh structure when combined with such ingredients.

14 Claims, 33 Drawing Sheets

Specification includes a Sequence Listing.

(56) References Cited

U.S. PATENT DOCUMENTS

| | | | |
|---|---|---|---|
| 7,654,998 | B1 | 2/2010 | Ingenito |
| 7,687,574 | B2 | 3/2010 | Lu et al. |
| 7,833,541 | B2 | 11/2010 | Lu et al. |
| 7,967,519 | B2 | 6/2011 | Gueret |
| 7,972,073 | B2 | 7/2011 | Vintimiglia |
| 8,104,985 | B2 | 1/2012 | Mancini et al. |
| 8,721,210 | B2 | 5/2014 | Wicyzynski |
| 2009/0071498 | A1 | 3/2009 | Tranchant |
| 2009/0155371 | A1 | 6/2009 | Sojka et al. |
| 2009/0220481 | A1 | 9/2009 | Maes et al. |
| 2011/0243983 | A1 | 10/2011 | Pautique |
| 2011/0256059 | A1 | 10/2011 | Sanchez Barreiro et al. |
| 2011/0262489 | A1 | 10/2011 | Zhao |
| 2012/0172457 | A1 | 7/2012 | Braun et al. |
| 2012/0279876 | A1 | 11/2012 | Weigel |
| 2012/0295870 | A1* | 11/2012 | Lebreton ............... C08J 3/24 514/54 |
| 2013/0224133 | A1* | 8/2013 | Romanhole ......... A61Q 19/005 424/59 |
| 2014/0147189 | A1 | 5/2014 | Wightman |
| 2014/0179640 | A1* | 6/2014 | Weinberger ........... A61K 9/107 514/159 |
| 2014/0193351 | A1* | 7/2014 | Mohammadi ........ A61K 8/9728 424/70.121 |
| 2015/0164770 | A1 | 6/2015 | Somerville et al. |
| 2015/0283055 | A1 | 10/2015 | Bonnet et al. |
| 2016/0030328 | A1 | 2/2016 | Mohammadi et al. |
| 2016/0174689 | A1 | 6/2016 | Wilczynski |

FOREIGN PATENT DOCUMENTS

| | | | |
|---|---|---|---|
| CN | 104473786 | | 4/2015 |
| CN | 104473786 A * | | 4/2015 |
| CN | 105233270 | | 1/2016 |
| CN | 105250184 | | 1/2016 |
| CN | 106137918 | | 11/2016 |
| CN | 106176688 | | 12/2016 |
| DE | 10-2008053905 | | 4/2015 |
| EP | 0516026 | | 12/1992 |
| EP | 1360955 | | 11/2003 |
| EP | 2798974 | | 11/2014 |
| FR | 2947727 A1 * | 1/2011 | ........... A61K 8/9794 |
| FR | 3028731 | | 5/2016 |
| FR | 3065358 | | 10/2018 |
| JP | S55-6582 | | 1/1980 |
| JP | S56-10805 | | 8/1981 |
| JP | 2001097888 A * | | 4/2001 |
| JP | 2004-016240 | | 1/2004 |
| JP | 2004/210765 | | 7/2004 |
| JP | 2004210765 A * | | 7/2004 |
| JP | 2007-536075 | | 12/2007 |
| JP | JP-2013-523227 | | 6/2013 |
| JP | 2004-000710 | | 1/2014 |
| JP | 2015-535307 | | 12/2015 |
| KR | 200365060 Y | | 10/2004 |
| KR | 10-2010-0087036 | | 8/2010 |
| WO | WO-99/53797 | | 10/1999 |
| WO | WO-2005/110024 | | 11/2005 |
| WO | WO-2009/079135 | | 6/2009 |
| WO | WO-2011/120535 | | 10/2011 |
| WO | WO-2014/044808 | | 3/2014 |
| WO | WO-2014043009 A1 * | 3/2014 | ............. A61P 43/00 |
| WO | WO-2016/062888 | | 4/2016 |
| WO | WO-2020181102 A1 * | 9/2020 | ........... C12N 15/113 |

OTHER PUBLICATIONS

FR-2947727-A1 (Google English Translation, downloaded Aug. 2021) (Year: 2021).*

Chun, et al.; Effect of molecular weight of hyaluronic acid (HA) on viscoelasticity and particle texturing feel of HA dermal biphasic fillers; Biomaterials Research; vol. 20; Article No. 24; pp. 1-7; Sep. 2016.

Goodman, et al; "An Interesting Reaction to a High and Low Molecular Weight Combination Hyaluronic Acid"; Letter and Communications; American Society for Dermatologic Surgery, Inc.; pp. S164-S166; 2015.

Lee, et al.; Effects of Low and High Molecular Weight Hyaluronic Acids on Peridural Fibrosis and Inflammation in Lumbar Laminectomized Rats; The Korean Journal of Pain; vol. 24; No. 4; pp. 191-198; Dec. 2011.

Lochhead, Robert Y; "Features Trends in Polymers for Skin Care, Part I"; HAPPI; 6 pps; Mar. 2009.

Mintel; http://www.gndp.com; Flash Dazzling Skin Ampoules; Record ID: 2542255; Laboratorious Marti Tor; Marti Derm La Formula; Skincare; Face/Neck Care; Spain; Jul. 2014.

Mintel; http://www.gnpd.com; Bio Cellulose Mask; Record ID: 2891365; It's More; Bio Suppu; Skincare; Face/Neck Care; Japan; Jan. 2015.

Mintel; http://www.gnpd.com; Black Rose Skin Regenerating Goodnight Mask; Record ID: 3453543; Krystyna Janda; Janda; Skincare; Face/Neck Care; Poland; Sep. 2015.

Mintel; http://www.gnpd.com; Boost Integral Revitalizing Supplement Serum: Record ID: 2751013; Immanence Integral Dermo Correction; IDC + Regen; Skincare; Face/Neck Care; France; Jul. 2015.

Mintel; http://www.gnpd.com; Face and Body Sunscreen Cream SPF 15; Record ID: 4166341; Planter's; Planter's Cosmetica Naturale Hyaluronic Acid Anti-Age; Skincare; Sun-Sun/Sunbed Exposure; Netherlands; Jul. 2016.

Mintel; http://www.gnpd.com; Instant Lifting Serum + Continual Integral Correction; Record ID: 3926305; Immanence Integral Dermo Correction; Immanence Integral Dermo Correction; IDC + Ideal Multi-Correction; Skincare; Face/Neck Care; France; May 2016.

Mintel; http://www.gnpd.com; Long Serum Mascara; Record ID: 2392551; Styling Life Holdings—Japan; Cayenne; Colour Cosmetics—Eye Colour Cosmetics—Eye Lash; Japan; May 2014.

Mintel; http://www.gnpd.com; Perfect Gel Foundation SPF40 PA+++; Record ID: 2882037; Dr. Ci;Labo; Dr. Ci:Labo; Colour Cosmetics; Face Colour Cosmetics—Foundations/Fluid Illuminators; Japan; Jan. 2015.

Mintel; http://www.gnpd.com; Perfect Water Cool SPF 50+/ PA++++; Record ID: 2661205; Isehan; Kiss Me by Isehan Sunkiller; Skincare; Sun—Sun/Sunbed Exposure; Japan; Feb. 2014.

Mintel; http://www.gnpd.com; S.O.S. Thirst-Quenching Serum; Record ID: 1787915; Caudalie; Caudalie Vinosource; Skincare; Face/Neck Care; USA; Apr. 2012.

PCT Int'l Search Report; Int'l Application No. PCT/US2017/064757; Completion Date: Feb. 27, 2018; dated Feb. 27, 2018.

PCT Int'l Search Report; Int'l Application No. PCT/US2017/064764; Completion Date: Apr. 18, 2018; dated Apr. 18, 2018.

PCT Written Opin of the Int'l Searching Authority; Int'l Application No. PCT/US2017/064757; Completion Date: Feb. 27, 2018; dated Feb. 27, 2018.

PCT Written Opin of the Int'l Searching Authority; Int'l Application No. PCT/US2017/064764; Completion Date: Apr. 18, 2018; dated Apr. 18, 2018.

Supplementary European Search Report: EP Application No. 17880149: Completion Date Oct. 29, 2019: dated Nov. 11, 2019.

Supplementary European Search Report: EP Application No. 17881085.9: Completion Date: Jan. 10, 2020; dated Jan. 24, 2020.

* cited by examiner

US 11,291,286 B2

SEQUENCE LISTING

```
<160> NUMBER OF SEQ ID NOS: 7

<210> SEQ ID NO 1
<211> LENGTH: 13
<212> TYPE: PRT
<213> ORGANISM: Artificial Sequence
<220> FEATURE:
<223> OTHER INFORMATION: CLOCK and/or PER1 gene activator
<220> FEATURE:
<221> NAME/KEY: misc_feature
<222> LOCATION: (1)..(4)
<223> OTHER INFORMATION: Xaa can be any naturally occurring amino acid
```

```
      or no amino acid
<220> FEATURE:
<221> NAME/KEY: misc_feature
<222> LOCATION: (5)
<223> OTHER INFORMATION: Xaa can be threonine or serine or no amino acid
<220> FEATURE:
<221> NAME/KEY: misc_feature
<222> LOCATION: (9)
<223> OTHER INFORMATION: Xaa can be isoleucine, leucine, proline,
      valine, alanine, glycine or no amino acid
<220> FEATURE:
<221> NAME/KEY: misc_feature
<222> LOCATION: (10)..(13)
<223> OTHER INFORMATION: Xaa can be any naturally occurring amino acid
      or no amino acid

<400> SEQUENCE: 1

Xaa Xaa Xaa Xaa Xaa Ser Thr Pro Xaa Xaa Xaa Xaa Xaa
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CLOCK and/or PER1 gene activator

<400> SEQUENCE: 2

Tyr Val Ser Thr Pro Tyr Asn
1               5

<210> SEQ ID NO 3
<211> LENGTH: 5
<212> TYPE: PRT
<213> ORGANISM: Artificial Sequence
<220> FEATURE:
<223> OTHER INFORMATION: CLOCK and/or PER1 gene activator

<400> SEQUENCE: 3

Val Ser Thr Pro Glu
1               5

<210> SEQ ID NO 4
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 4

Leu His Ser Thr Pro Pro
1               5

<210> SEQ ID NO 5
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 5

Arg His Ser Thr Pro Glu
1               5

<210> SEQ ID NO 6
<211> LENGTH: 5
<212> TYPE: PRT
<213> ORGANISM: Artificial Sequence
<220> FEATURE:
```

-continued

```
<223> OTHER INFORMATION: CLOCK and/or PER1 gene activator

<400> SEQUENCE: 6

His Ser Thr Pro Glu
1               5

<210> SEQ ID NO 7
<211> LENGTH: 4
<212> TYPE: PRT
<213> ORGANISM: Artificial Sequence
<220> FEATURE:
<223> OTHER INFORMATION: CLOCK and/or PER1 gene activator

<400> SEQUENCE: 7

Ser Pro Leu Gln
1
```

COSMETIC COMPOSITIONS WITH A MICRO-MESH STRUCTURE

RELATED APPLICATIONS

This application is a continuation of U.S. patent application Ser. No. 15/832,493, filed Dec. 5, 2017, which claims the benefit of U.S. Provisional Patent Application No. 62/434,717, filed Dec. 15, 2016, each of which is incorporated by reference herein in its entirety.

The content of the ASCII text file of the sequence listing name "16-53-2C1_seqlist", which is 1.94 KB in size and was created on and electronically submitted via EFS-Web on Jul. 14, 2020, is incorporated herein by reference in its entirety. Please replace the existing Sequence Listing for the above-referenced application with the Substitute Sequence Listing submitted herewith.

TECHNICAL FIELD

The invention is in the field of cosmetic compositions for topical application to keratin surfaces for providing benefits such as improving the integrity and thickness of the stratum corneum and promoting skin health and wellness.

BACKGROUND OF THE INVENTION

Skin has two major layers: the epidermis and the dermis. The epidermis is the outer most layer of skin. The dermis is the lower layer of skin that contains collagen and elastin fibers that provide strength to skin and where skin vasculature and nerves are found. The epidermis has five layers. The outermost layer is the stratum corneum, followed by the stratum lucidum, stratum granulosum, stratum spinosum, and, finally the stratum basale as the deepest layer next to the dermis. The stratum basale contains cells that continuously divide and form new keratinocytes to replace those that are being shed. The stratum basale also contains melanocytes that produce skin color. The stratum spinosum contains the keratin producing cells that were formed in the stratum basale. The stratum granulosum is where keratin and other biological materials are produced that help to waterproof skin. The stratum lucidum is found in thicker skin and is formed of flattened dead cells. It reduces friction between stratum corneum and stratum granulosum.

The stratum corneum is largely responsible for skin barrier function. It was once believed that the stratum corneum was biologically inert. However, it is now recognized that it has an intricate chemical and physical biology despite the fact that the corneocytes (keratinocytes that have become cornified) which make it up are dead cells. Maintaining a healthy stratum corneum is vital to achieving healthy skin and its associated attractive appearance.

The structure of the stratum corneum has often been analogized to a "brick and mortar" type of construction with corneocytes forming the bricks. About 12 to 16 layers of corneocytes form a protein complex with an organized matrix comprised of threads of keratin that can retain considerable amounts of water between the threads. In general, each corneocyte has a diameter of about 1 micron which may vary depending on the individual's age, exposure to environmental conditions, or other factors. Keratinocytes proliferate in the stratum basale and migrate through the layers of the epidermis to the skin surface and replace keratinocytes that become cornified. While the keratinocytes migrate through the stratum spinosum and stratum granulosum, lamellar bodies are formed within. When they mature to the stratum corneum, enzymes degrade the outer envelope of the lamellar bodies to release free fatty acids and ceramides to fuse together in the stratum corneum to form a cornified envelope containing a continuous layer of lipids. Because there are two types of lipids, this layer is referred to as a lamellar lipid bilayer. This bilayer plays a major role in maintaining the barrier properties of skin and is often referred to as the mortar component in the brick and mortar analogy. Corneocytes are surrounded by a cell envelop that is composed primarily of proteins loricirn and involucrin that contain extensive linkages that create an insoluble barrier. Attached to the cell envelope is a layer of ceramide lipids that repel water. Because the lamellar lipid bilayer also repels water, water molecules are held between the cell envelope lipids and the lipid bilayer. This helps maintain the water balance in the stratum corneum by trapping water molecules instead of letting them absorb into the lower layers of the epidermis. These proteins contain extensive links between each other making the cell envelope the most insoluble structure of the corneocyte. The "rivets" that hold the corneocytes together are specialized protein structures called corneodesmosomes, which are the major structures that must be degraded for the skin to shed in a process called desquamation. Natural moisturizing factor (NW) is a collection of water-soluble compounds that are only found in the stratum corneum. These compounds comprise approximately 20 to 30 percent of the dry weight of the corneocyte. NMF components absorb water from the atmosphere and combine it with their own water content allowing the outermost layers of the stratum corneum to stay hydrated despite exposure to the elements. Because NMF components are water-soluble, they are easily leached from the cells with water contact, which is why repeated contact with water actually makes the skin drier. The lipid layer surrounding the corneocyte helps seal the corneocyte to prevent loss of NMF.

The desquamation or exfoliation process of the stratum corneum is actually very complex and only parts of this process are fully understood. It is known that several enzymes degrade the corneodesmosomes in a specific pattern. While water and pH are known to play a significant role in the activation of enzymes necessary to start the exfoliation process, the exact nature of the enzymes and the activation necessary to start the exfoliation process still remains unknown.

Accordingly, there is great interest in formulating products for topical application to skin that will correct, supplement, and maintain skin barrier function, minimize loss of NMF, and supplement the skin's natural biological process of keratinocyte generation and cornification in order to optimize the appearance of heathy skin.

It has been discovered that the stratum corneum and underlying layers of the epidermis can be significantly strengthened and thickened by formulating topical products that contain certain ingredients that interact with each other to form a micro-mesh-like structure in the form of three dimensional structures of interlocked spheres that are associated with each other to form a network.

SUMMARY OF THE INVENTION

The invention is directed to a topical composition comprising:
   a Polymer (as defined in Section II below),
   a high molecular weight hyaluronic acid (HWM HA) and/or its salt,
   a low molecular weight hyaluronic acid (LWM HA) and/or its salt, and a polyamino acid and/or its salt; and
water.

The invention also directed to method for formulating a topical composition containing a micro-mesh (as defined below) comprising the steps of:

Combining a test polymer with at least one LWM HA, at least one HWM HA, a polyamino acid salt, and water;

Using SEM to determine whether a micro-mesh is formed, selecting the polymer that forms a micro-mesh; and formulating a topical product that contains the same combination of ingredients that forms the micro-mesh in the same ratios and percentages as are found when the test polymer, LMW HA, HMW HA, polyamino acid, and water alone are combined.

DETAILED DESCRIPTION

I. Definitions

Figure 1A:
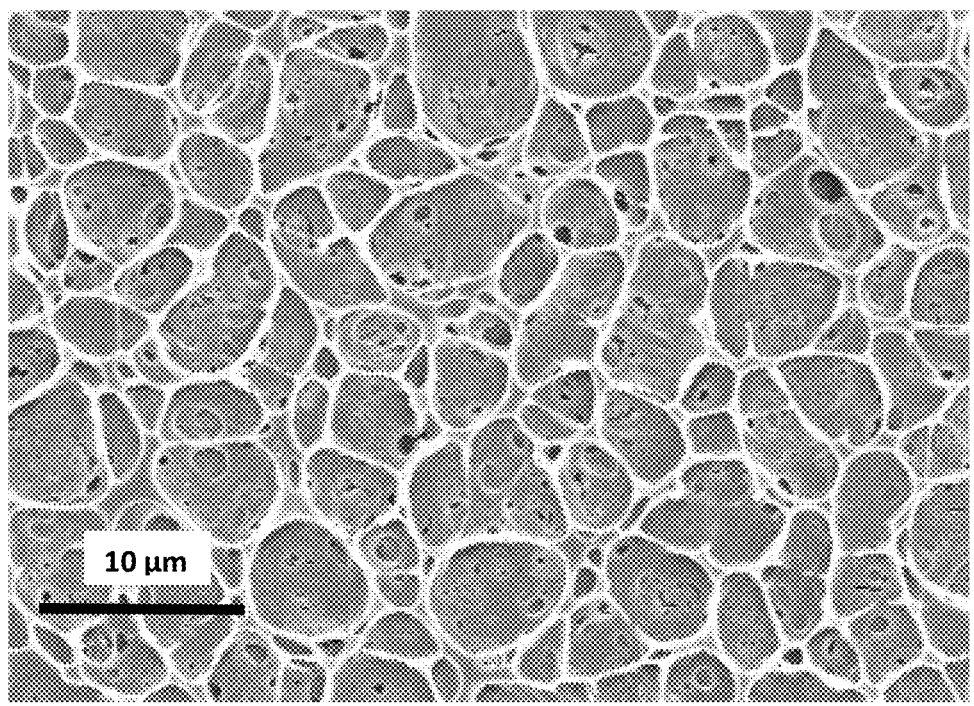
FIG. 1A: shows a SEM image of the Micro-Mesh hydrogel made in Example 1.

All percentages mentioned herein are percentages by weight unless otherwise indicated.

All documents mentioned herein are incorporated by reference in their entirety.

"Autophagy" means the process by which cells cleanse themselves of toxins and debris by forming a membrane around the debris, segregating it from the rest of the cell, and adjoining the formed vacuole with cellular lysosomes, which are cellular organelles that contain acid hydrolase enzymes that break down the cellular debris and waste found in the vacuole.

"Autophagy Activator" means an ingredient that stimulates the normal cellular autophagy processes.

"CLOCK gene activator" means an ingredient that activates one or more CLOCK genes present in keratinocytes.

The term "DNA repair enzyme" means an enzyme that is operable to repair DNA base mutagenic damage. Such enzymes are often categorized by the type of DNA damage they repair, for example BER (base excision repair) enzymes, nucleotide excision repair (NER) enzymes; mismatch repair (MMR) enzymes; DNA helicases; DNA polymerases, and so on. For example, mutations such as 8-oxo-7,8-dihydro-2'-deoxyguanosine may be repaired by OGG1 (8-oxoGuanine glycosylase); T-T dimers which may be repaired by (Nucleotide excision repair (NER) Photolyase); 6-4 photoproducts (which may be repaired by NER); and 06-methyl guanine (which may be repaired by 06-alkyl guanine transferase (AGT)).

"Micro-mesh" means three dimensional spherical structures having membranous outer walls that are interlocked in association to form a network. The membranous outer walls of the spherical structure form an internal space within the sphere that is secluded from the surrounding environment and the contents of the interlocked spheres. In one preferred embodiment, from about 80 to 90% of the spherical structures formed when combining the Polymer, LMW HA, HMW HA, polyamino acid salt and water have a two dimensional area ranging from 0.001 to 1000 um$^2$ diameter ranging from 0.001 to 50 microns.

The term "hydrogel" means the gel that is formed when water is added to the mixture of the Polymer, LMW HA, HMW HA, and polyamino acid salt where the water will fill the spaces between the three dimensional spheres that are formed causing a gel to form.

The term "Scanning Electron Microscope (SEM)" means that a microscope scans a sample with a focused electron beam and delivers images with information about the sample topography and composition.

"PER1 gene activator" means an ingredient that activates one or more PER1 genes found in keratinocytes.

"Proteasome" means a protein complex typically located in the nucleus or cytoplasm of cells that is operable to degrade damaged cellular proteins by proteolysis into smaller subunits which may then be further digested into single amino acids. These recycled amino acids may be used by the cell in the synthesis of new proteins.

"Proteasome activator" means an active ingredient that stimulates the activity of proteasomes in cells of keratin surfaces such as keratinocytes, fibroblasts, etc.

"Recycle" means, with respect to the degradation of cellular debris and toxins, that the debris and toxins may be broken down into molecules such as proteins, lipids, amino acids, or other biological materials that are usable by the cell in its normal healthy metabolic processes.

"Repair" means, with respect to skin cells, that the damaged portions of cells, such as DNA, mitochondria, proteins, lipids, or other cellular materials are reduced or eliminated.

"Selective catabolysis" means, with respect to the cells of keratin surfaces, that the cells are able to cleanse themselves of debris, waste, and toxins selectively without compromising healthy cellular constituents, and preferably by one or more of mechanisms such as activating cellular autophagy or activating cellular proteasome processes.

II. The Topical Composition

The topical composition comprises the ingredients set forth below. The topical composition may be in the form of an emulsion, aqueous solution or dispersion, gel, or anhydrous composition. If in the form of an emulsion, it may be a water in oil or oil in water emulsion. If in the form of an emulsion, the composition may contain from about 1-99%, preferably from about 5-90%, more preferably from about 10-85% water and from about 1-99%, preferably from about 5-90%, more preferably from about 5-75% of oil. If in the form of an aqueous suspension or dispersion, the composition may generally contain from about 1-99.9%, preferably from about 5-95%, more preferably from about 10-90% water, with the remaining ingredients being the active ingredients or other formula ingredients.

A. The Polymer (the "Polymer")

The topical composition comprises at least one Polymer as further defined herein. Suggested amounts of the Polymer may range from 0.001 to 10%, preferably 0.01 to 5% and more preferably 0.05 to 1.0% by the weight of total composition. In addition to the Polymers recited below, other suitable polymers that form the desired micro-mesh structure can be identified by combining the test polymer with LMW HA, HMW HA, the polyamino acid, and water and ascertaining whether the combined ingredients form a micro-mesh as defined herein and as demonstrated in the drawings.

Reference to the Polymer, LMW HA, HMW HA, and polyamino acid will also include the corresponding alkali metal or alkaline earth metal salts including but not limited to sodium, potassium, and the like.

(1) Water Absorbing Acrylic or Methacrylic Resins

One suitable polymer is a water-absorbing polymer as disclosed in U.S. Patent Application Publication No. 2016-0030328. This polymer may be obtained from the polymerization of monomers (A), (B) and (C):

(i) Component (A) is a phosphate-containing acrylic or methacrylic monomer. As long as a monomer has a phosphate group and an acrylic or methacrylic group, the structure of a linkage for connecting these two groups is not particularly limited. Exemplary linkages include alkylene groups such as methylene, ethylene and propylene and oxyalkylene groups such as oxyethylene, oxypropylene, oxybutylene, oxypentamethylene and mixtures thereof. Of these, polyoxyalkylene groups are preferred, with polyoxypropylene being most preferred. The monomer is commercially available, for example, under the tradename of Sipomer PAM-200 from Rhodia.

Also included is a salt of a phosphate-containing acrylic or methacrylic monomer, which may be formed by adding an alkaline aqueous solution to the phosphate-containing acrylic or methacrylic monomer.

(ii) Component (B) is a monomer having one acrylic or methacrylic group within the molecule other than component (A). Suitable monomers include acrylic acid, methacrylic acid, maleic acid, maleic anhydride, fumaric acid, crotonic acid, itaconic acid, 2-(meth)acrylamide-2-methylpropanesulfonic acid, (meth)acryloxyalkanesulfonic acid, N-vinyl-2-pyrrolidone, N-vinylacetamide, (meth)acrylamide, N-isopropyl(meth)acrylate, N,N-dimethyl(meth)acrylamide, 2-hydroxyethyl(meth)acrylate, methoxypolyethylene glycol(meth)acrylate, polyethylene glycol(meth)acrylate, and stearyl acrylate. A salt of the monomer may be formed by adding an alkaline aqueous solution to the (meth)acrylic monomer.

The "salt" includes alkali metal salts such as sodium, potassium and lithium, alkaline earth metal salts such as calcium, magnesium and barium, and ammonium salts such as quaternary ammonium and quaternary alkyl ammonium. Inter alia, sodium salt is the most common and preferred. Neutralization treatment is preferably carried out at a temperature of 10 to 100° C., more preferably 20 to 90° C. Acrylic acid or polyacrylic acid following polymerization may be neutralized with a base. Neutralization prior to polymerization is preferred because it is time consuming to post-neutralize non-neutralized or low-neutralized (specifically a degree of neutralization of less than 30 mol %) polyacrylic acid following polymerization. The water-absorbing polymer of the invention preferably has a degree of neutralization of 0.01 to 100%, more preferably 1 to 90%, and even more preferably 20 to 80% based on the moles of acid groups in the polymer.

(iii) Component (C) is an organopolysiloxane having a (meth)acrylic group at both ends, represented by the general formula (1):

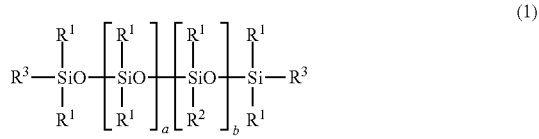

wherein $R^1$ is each independently an aliphatic unsaturation-free monovalent hydrocarbon group having 1 to 8 carbon atoms. $R^2$ is a group containing a polyoxyalkylene group having the general formula (2):

wherein $R^4$ is each independently a divalent organic group having 2 to 15 carbon atoms, x and y each are an integer of 0 to 30, meeting $1 \leq x+y \leq 50$, $R^3$ is a substituent group having a (meth)acrylic group, a is an integer inclusive of 0 and b is an integer of at least 1.

Examples of the monovalent hydrocarbon group represented by $R^1$ include alkyl groups such as methyl, ethyl and butyl, cycloalkyl groups such as cyclopentyl and cyclohexyl, aryl groups such as phenyl and tolyl, and aralkyl groups such as benzyl and phenethyl. Inter alia, alkyl groups of 1 to 4 carbon atoms and phenyl are preferred, with methyl being most preferred.

In formula (2), $R^4$ is each independently selected from divalent organic groups having 2 to 15 carbon atoms, for example, $-(CH_2)_2-$, $-(CH_2)_3-$, $-(CH_2)_4-$, $-CH_2CH(CH_3)CH_2-$, $-(CH_2)_8-$, and $-(CH_2)_{11}-$. Inter alia, $-(CH_2)_2-$, $-(CH_2)_3-$, and $-(CH_2)_4-$ are preferred. Each of x and y is an integer of 0 to 30, meeting $1 \leq x+y \leq 50$. Preferably each of x and y is an integer of 5 to 25, more preferably 10 to 20, and the sum of x+y is 10 to 45, more preferably 20 to 40.

A preferred suitable water-absorbing polymer is Sodium Polyacrylate Crosspolymer-1, which is a crosslinked polymer that is obtained by the polymerization of methacrylic acid and methacryloyl PPG-6 phosphate and a silicone copolymer prepared by reacting a methacrylate-terminated polydimethylsiloxane polymer containing silicon hydride groups with PEG-18/PPG-17 allyl ether.

(2) Copolymers of Acryloyldimethyltaurate

Also suitable is a thickening polymer obtained from the polymerization of partially salified or completely salified 2-methyl 2-[(1-oxo 2-propenyl) amino]1-propanesulfonic acid, with at least one neutral monomer selected from acrylamide, (2-hydroxy-ethyl) acrylate or N,N-dimethyl acrylamide, and at least one monomer of formula (I):

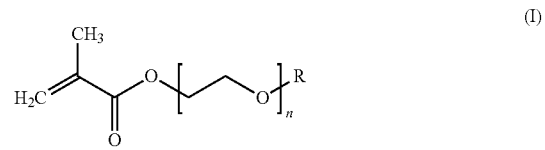

in which R represents a linear or branched alkyl radical having from eight to twenty carbon atoms and n represents a number greater than or equal to one and less than or equal to twenty, selected from tetraethoxylated lauryl methacrylate or eicosaethoxylated stearyl methacrylate in the presence of at one crosslinking agent. This polymer is set forth in U.S. Patent Application Publication No. 2012/0172457 also hereby incorporated by reference in its entirety.

One preferred suitable thickening polymer is a copolymer of ammonium acryloyldialkyltaurate, dialkylacrylamide, lauryl methacrylate and laureth-4 methacrylate, crosslinked with trimethylolpropane triacrylate.

Most preferred is a polymer having the INCI name Polyacrylate Crosspolymer-6 that may be purchased from Seppic Inc under the tradename SepiMAX Zen. Polyacrylate crosspolymer-6 is a copolymer of ammonium acryloyldimethyltaurate, dimethylacrylamide, lauryl methacrylate and laureth-4 methacrylate, crosslinked with trimethylolpropane triacrylate.

(3) Acrylate Crosslinked Silicone Copolymers

Also suitable are acrylate crosslinked silicone copolymers that contain at least one polyether substituted structure unit and at least one epoxy or oxirane structural unit reacted with acrylates to produce crosslinked silicones containing polyether substituted structural networks and acrylate crosslinks. Such polymers are disclosed in U.S. Pat. Nos. 7,687,574 and 7,833,541 which are hereby incorporated by reference in the entirety.

In particular, the polymer may be the reaction product of:
1) $M_a M^H_{b-h-k} M^{PE}_h M^E_k D_c D^H_{d-i-l} D^{PE}_i D^E_l T_e T^H_{f-j-m} T^{PE}_j T^E_m Q_g$ and
2) a stoichiometric or super-stoichiometric quantity of acrylate where $M=R^1R^2R^3SiO_{1/2}$;

$M^H=R^4R^5HSiO_{1/2}$;

$M^{PE}=R^4R^5(-CH_2CH(R^9)(R^{10})_nO(R^{11})_o(C_2H_4O)_p (C_3H_6O)_q(C_4H_8O)_rR^{12})SiO_{1/2}$;

$M^E=R^4R^5(-R^{17}R^{18}C-CR^{16}Q_sQ_rR^{15}(COC)R^{13}R^{14}) SiO_{1/2}$ $D=R^6R^7SiO_{2/2}$; and $D^H=R^8HSiO_{2/2}$ $D^{PE}=R^8(-CH_2CH(R^9)(R^{10})_nO(R^{11})_o(C_2H_4O)_p (C_3H_6O)_q(C_4H_8O)_rR^{12})SiO_{2/2}$ $D^E=R^8(-R^{17}R^{18}C-CR^{16}Q_sQ_rR^{15}(COC)R^{13}R^{14}) SiO_{2/2}$.

$T=R^{19}SiO_{3/2}$;

$T^H = HSiO_{3/2}$;

$T^{PE} = (-CH_2CH(R^9)(R^{10})_nO(R^{11})_o(C_2H_4O)_p(C_3H_6O)_q(C_4H_8O)_rR^{12})SiO_{3/2}$;

$T^E = (-R^{17}R^{18}C-CR^{16}Q_sQ_tR^{15}(COC)R^{13}R^{14})SiO_{3/2}$; and $Q = SiO_{4/2}$;

where $R^1$, $R^2$, $R^3R^4$, $R^5$, $R^6$, $R^7$, $R^8$ and $R^{19}$ are each independently selected from the group of monovalent hydrocarbon radicals having from 1 to 60 carbon atoms;

$R^9$ is H or a 1 to 6 carbon atom alkyl group; $R^{10}$ is a divalent alkyl radical of 1 to 6 carbons;

$R^{11}$ is selected from the group of divalent radicals consisting of $-C_2H_4O-$, $-C_3H_6O-$, and $-C_4H_8O-$; $R^{12}$ is H, a monofunctional hydrocarbon radical of 1 to 6 carbons, or acetyl; $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_t$ is a di- or trivalent hydrocarbon radical having from one to sixty carbon atoms, $Q^s$ is a divalent hydrocarbon radical having from one to sixty carbon atoms subject to the limitation that when $Q_t$ is trivalent $R^{14}$ is absent and $R^{16}$ and $R^{18}$ may be either cis- or trans- to each other;

the subscript a may be zero or positive subject to the limitation that when the subscript a is zero, b must be positive;

the subscript b may be zero or positive subject to the limitation that when b is zero, the subscript a must be positive;

the subscript c is positive and has a value ranging from about 5 to about 1,000;

the subscript d is positive and has a value ranging from about 3 to about 400;

the subscript e is zero or positive and has a value ranging from 0 to about 50;

the subscript f is zero or positive and has a value ranging from 0 to about 30;

the subscript g is zero or positive and has a value ranging from 0 to about 20;

the subscript h is zero or positive and has a value ranging from 0 to about 2 subject to the limitation that the sum of the subscripts h, i and j is positive;

the subscript i is zero or positive and has a value ranging from 0 to about 200 subject to the limitation that the sum of the subscripts h, i and j is positive;

the subscript j is zero or positive and has a value ranging from 0 to about 30 subject to the limitation that the sum of the subscripts h, i and j is positive;

the subscript k is zero or positive and has a value ranging from 0 to about 2 subject to the limitation that the sum of the subscripts k, l and m is positive;

the subscript l is zero or positive and has a value ranging from 0 to about 200 subject to the limitation that the sum of the subscripts k, l and m is positive;

the subscript m is zero or positive and has a value ranging from 0 to about 30 subject to the limitation that the sum of the subscripts k, l and m is positive;

the subscript n is zero or one;
the subscript o is zero or one;
the subscript p is zero or positive and has a value ranging from 0 to about 100 subject to the limitation that $(p+q+r)>0$;
the subscript q is zero or positive and has a value ranging from 0 to about 100 subject to the limitation that $(p+q+r)>0$;
the subscript r is zero or positive and has a value ranging from 0 to about 100 subject to the limitation that $(p+q+r)>0$;
the subscript s is zero or one;
the subscript t is zero or one; and
3) a free radical initiator.

A preferred suitable polymer is Polyacrylate Crosspolymer-7, which is a copolymer of methacrylate PPG-6 phosphate and one or more monomers of acrylic acid, methacrylic acid or one of their simple esters, crosslinked with dimethicone PEG/PPG-25/29 acrylate.

(4) Anionic Polysaccharides

Also suitable are one or more naturally derived anionic polysaccharides including alginic acid or its sodium salt.

A more preferred suitable natural anionic polysaccharide is sodium alginate.

B. The Low and High Molecular Weight Hyaluronic Acids

The cosmetic composition comprises at least one LMW HA and at least one HMW HA. Preferably the weight ratio of LMA HA to BMW HA may range from about 100:1 to 1:100, preferably about 50:1 to 1:50, more preferably about 15:1 to 1:15.

(1) High Molecular Weight Hyaluronic Acid

The HMW HA has a molecular weight ranging from about $8 \times 10^5$ Dalton to $1 \times 10^7$ Dalton, preferably from $1 \times 10^6$ Dalton to $8 \times 10^6$ Dalton, more preferably from $1.2 \times 10^6$ Dalton to $3 \times 10^6$ Dalton. The BMW HA may be synthetic or it may be obtained by biotechnological processing by fermenting yeasts such as saccharomyces in fermentation processes. A suitable HMW HA for use in the claimed composition may be purchased from Contipro Biotech s.r.o. under the name Hyaluronic Acid, Sodium Salt which has the INCI name Sodium Hyaluronate.

Suggested ranges of HMW HA may range from about 0.001 to 10%, preferably about 0.005 to 5% and more preferably about 0.01 to 1.5% by weight of the total composition.

(2) Low Molecular Weight Hyaluronic Acids (LMW HA)

The molecular weight of the LMA HA or its salt may range from about $1 \times 10^3$ Dalton to $8 \times 10^5$ Dalton, preferably from $5 \times 10^3$ Dalton to $1 \times 10^5$ Dalton, more preferably from $8 \times 10^3$ Dalton to $5 \times 10^4$ Dalton. The LMW HA may also be synthetic or it may be obtained by biotechnological processing by fermenting yeasts such as saccharomyces from fermentation processes. A suitable hyaluronic acid for use in the claimed composition may be purchased from Contipro Biotech s.r.o. under the name HyActive powder which has the INCI name Sodium Hyaluronate.

Suggested ranges of LMW HA range from about 0.001 to 10%, preferably about 0.005 to 5% and more preferably about 0.01 to 1.5% by weight of the total composition.

C. Amino Acid Homo- or Copolymers or Salts Thereof

The cosmetic composition comprises at least one polymer comprised of a polyamino acid and/or its salt. Suggested ranges of the polyamino acid range from about 0.001 to 10%, preferably 0.005 to 5% and more preferably 0.01 to 1% by weight of the total composition. Such polymers include those disclosed in U.S. Pat. No. 3,867,352.

Most preferred is a polymer of aspartic acid, sodium salt having the repeat units:

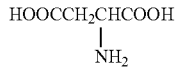

Most preferred is a polymer having the INCI name Sodium Polyaspartate having a molecular weight ranging from 2,000 to 6,000 Daltons, more preferably 3,000 to 5,000 Daltons. This polymer may be purchased from Ajinomoto under the tradename Aquadew SPA-30.

III. Other Ingredients

The topical composition may contain other ingredients including but not limited to those set forth herein.

A. Autophagy Activator

The composition of the invention may contain one or more ingredients that are operable to activate normal cellular autophagic processes. The autophagy activator is present in amounts ranging from about 0.00001 to 20%, preferably 0.0001-5%, more preferably from about 0.001 to 1%. In general, the cellular autophagy process comprises four general steps. Step 1 is the initiation of vacuole formation; Step 2 the formation of the initial vacuole or autophagosome which sequesters the cytoplasmic material to be degraded. Step 3 is the maturation of the autophagosome into a degradative vacuole. Step 4 is the actual degradation of the sequestered material.

Ingredients with autophagy activation activity can be identified by their ability to either stimulate or inhibit various cellular metabolic pathways. For example, ingredients that stimulate the expression of MAP-LC3, ATGS-12, protein p53, AMPK, or DRAM are suitable autophagy activators. Ingredients that inhibit the expression of mTOR are also suitable autophagy activators.

The gene MAP-LC3 codes for microtubule-associated protein 1 light chain 3, a protein that initiates formation of autophagosomes. ATGS-12 also stimulates formation of autophagosomes. mTOR, also known as mammalian target of rapamycin, is also known as the mechanistic target of rapamycin or FK506 binding protein 12-rapamycin associated protein 1 (FRAP1). FRAP1 is encoded by the FRAP gene. Any ingredient that inhibits the expression of mTOR, involved in autophagosome creation, will have autophagy activating properties. Also suitable as autophagy activators are ingredients that stimulate expression of protein p53, AMPK, and/or DRAM (damage remedy autophagy modulator protein) in keratinocytes. Protein p53, also known as a tumor suppressor protein, is encoded by the p53 gene. AMPK means AMP activated protein kinase and DRAM, damage related autophagy modulator. Both are known to stimulate autophagy activation in keratinocytes.

Thus any ingredient that has the above mentioned effects on the genes may be suitable autophagy activators. During the autophagocytic process cellular debris such as oxidized proteins and peroxidized lipids are degraded. Such cellular debris often affects normal metabolic function. Screening of ingredients to determine efficacy by ability to stimulate or inhibit cellular, preferably keratinocyte, genes and/or proteins mentioned above may be done according to methods as set forth in US Patent Publication No. 2011/0243983 or other methods known in the art.

For example, one general process for identifying ingredients that may be autophagy activators is by first inducing nutritive stress in cultured cells such as keratinocytes. For example, the cells are first cultured in complete culture medium with growth factors, for about 24 hours. The culture medium is then removed and replaced with a non-nutritive culture medium, for example one that does not contain growth factors. The cells are cultured for about 30 minutes to about 25 hours in a state of nutritive stress. Then, the non-nutritive culture medium is removed and replaced with complete culture medium to promote cellular recovery. Thereafter, the cells are evaluated for autophagocytic activity by measuring the expression of one or more of MAP-LC3; ATGS-12; phosphorylated mTOR; phosphorylated p53; DRAM; or phosphorylated AMPK in those cells. Measurement of such expression can take place by immunofluorescence measurements. In addition, the expression can be ascertained by Western Blot analysis of phosphorylated proteins associated with the expressed genes.

Examples of ingredients that are known to exert either the stimulatory or inhibitory effects on the above mentioned genes which, in turn, stimulate autophagy, are yeast extracts including but not limited to those from the genuses such as *Lithothamnium, Melilot, Citrus, Candida, Lens, Urtica, Carambola, Momordica, Yarrowia, Plumbago*, etc. Further specific examples include *Lithothamniumn calcareum, Melilotus officinalis, Citrus limonum, Candida saitoana, Lens culinaria, Urtica dioica, Averrhoa carambola, Momordica charantia, Yarrowia lipolytica, Plumbago zeylanica* and so on.

Also suitable are ingredients such as amiodarone hydrochloride, GF 109203X which is also referred to as (3-(N-[Dimethylamino]propyl-3-indolyl)-4-(3-indolyl)maleimide 3-[1-[3-(Dimethylamino)propyl]1H-indol-3-yl]-4-(1H-indol-3-yl)1H-pyrrole-2,5 dione Bisindolylmaleimide I; N-Hexanoyl-D-sphingosine; Niclosamide; Rapamycin from *Streptomyces hygroscopicus*; Rottlerin which is also referred to as (1-[6-[(3-Acetyl-2,4,6-trihydroxy-5-methylphenyl) methyl]-5,7-dihydroxy-2,2-dimethyl-2H-1-benzopyran-8-yl]-3-phenyl-2-propen-1-one, Mallotoxin); STF-62247, also known as 5-Pyridin-4-yl-thiazol-2-yl-m-tolyl-amine; Tamoxifen; Temsirolimus which is also known as 42-[3-Hydroxy-2-methylpropanoate, CCI-779, Rapamycin; ATG1 autophagy related 1 homolog; ATG1, Serine/threonine-protein kinase ULK1, UNC-51-like kinase; or Z36 which is also referred to as ((Z)-5-Fluoro-1-(3'-dimethylamino)propyl-3-[(5'-methoxyindol-3-ylidene)methyl]-indolin-2-one; or 1-[3-(dimethylamino)propyl]-5-fluoro-1,3-dihydro-3-[(5-methoxy-1H-indol-3-yl)methylene]-2H-Indol-2-one); Bufalin, also referred to as 3β,14-Dihydroxy-5β,20(22)-bufadienolide, 5β,20(22)-Bufadienolide-3β,14-diol. Such ingredients may be purchased from Sigma-Aldrich Chemical Company.

B. Proteasome Activator

The composition may contain one or more proteasome activators in an amount ranging from about 0.0001 to 65%, preferably from about 0.0005 to 50%, more preferably from about 0.001 to 40%.

Suitable proteasome activators are any compounds, molecules, or active ingredients that stimulate proteasome activity in the cells of keratin surfaces.

Examples of suitable proteasome activators include, but are not limited to, algin, alginates, hydrolyzed algin, molasses extract, *Trametes* extracts, including extracts from *Trametes versicolor*, olea hydroxol.

C. CLOCK, PER1 Gene Activator

The composition of the invention may contain a CLOCK or PER1 cellular gene activator. Suggested ranges are from about 0.000001 to about 40%, preferably from about 0.000005 to 35%, more preferably from about 0.00001 to 25%. Suitable CLOCK or PER1 activators may be present in the form of botanical extracts, polypeptides, peptides, amino acids, and the like.

1. Peptide CLOCK or PER1 Gene Activator

A particularly preferred CLOCK and/or PER1 gene activator comprises a peptide of the formula (I):

$$R_1\text{-}(AA)_n\text{-}X_1\text{—}S\text{-}T\text{-}P\text{—}X_2\text{—}(SS)_p\text{—}R_2$$

where $(AA)_n\text{-}X_1\text{—}S\text{-}T\text{-}P\text{—}X_2\text{-}(AA)_p$ is (SEQ ID No. 1), and:

$X_1$ represents a threonine, a serine, or is equal to zero, $X_2$ represents an isoleucine, leucine, proline, valine, alanine, glycine, or is equal to zero, AA represents any amino acid or derivative thereof, and n and p are whole numbers between 0 and 4, $R_1$ represents the primary amine function of the N-terminal amino acid, either free or substituted by a protective grouping that may be chosen from either an acetyl group, a benzoyl group, a tosyl group, or a benzyloxycarbonyl group, $R_2$ represents the hydroxyl group of the carboxyl function of the C-terminal amino acid, substituted by a protective grouping that may be chosen from either a C1 to C20 alkyl chain or an $NH_2$, NHY, or NYY group with Y representing a C1 to C4 alkyl chain, wherein the sequence of general formula (I) comprises from about 3 to 13 amino acid residues, said sequence of general formula (I) possibly containing substitutions of amino acids $X_1$ and $X_2$ with other chemically equivalent amino acids; wherein the amino acids are: Alanine (A), Arginine (R), Asparagine (N), Aspartic Acid (D), Cysteine (C), Glutamic Acid (E), Glutamine (Q), Glycine (G), Histidine (H), Isoleucine (I), Leucine (L), Lysine (K), Methionine (M), Phenylalanine (F), Proline (P), Serine (S), Threonine (T), Tryptophan (W), Tyrosine (Y), Valine (V). More preferred, are peptides of the above formula, as follows:

S-T-P-NH₂

Ser-Thr-Pro-NH₂

(SEQ ID No. 2)

Y-V-S-T-P-Y-N-NH₂

Tyr-Val-Ser-Thr-Pro-Tyr-Asn-NH₂

(SEQ ID NO. 3)

NH₂-V-S-T-P-E-NH₂

NH₂-Val-Ser-Thr-Pro-Glu-NH₂

(SEQ ID No. 4)

NH₂-L-H-S-T-P-P-NH₂

NH₂-Leu-His-Ser-Thr-Pro-Pro-NH₂

(SEQ ID No. 5)

CH₃NH-R-H-S-T-P-E-NH₂

CH₃-NH-Arg-His-Ser-Thr-Pro-Glu-NH₂

(SEQ ID No. 6)

CH₃NH-H-S-T-P-E-CH₃NH

CH₃-NH-His-Ser-Thr-Pro-Glu-CH₃-NH especially S-T-P—NH₂, or NH₂-L-H—S-T-P—P—NH₂ (SEQ ID No. 4), or mixtures thereof. S-T-P—NH₂ is available from ISP-Vinscience under the trademark Chronolux® and having the INCI name Tripeptide-32. Also highly preferred is (SEQ ID No. 7)

S-P-L-Q-NH₂

Ser-Pro-Leu-Gln-NH₂ a peptide manufactured by ISP-Vinscience under the trademark Chronogen® and having the INCI name Tetrapeptide-26.

2. Botanical Extracts

Also suitable as the CLOCK or PER1 gene activator is cichoric acid or isomers or derivatives thereof. Cichoric acid may be synthetic or naturally derived. Synthetic cichoric acid may be purchased from a number of commercial manufacturers including Sigma Aldrich. Cichoric acid may also be extracted from botanical sources that are known to contain cichoric acid such as *Echinacea, Cichorium, Taraxacum, Ocimum, Melissa*, or from algae or sea grasses. More specifically, botanical extracts such as *Echinacea purpurea, Cichorium intybus, Taraxacum officinale, Ocimum basilicum*, or *Melissa officinalis*. The term "cichoric acid" when used herein also includes any isomers thereof that are operable to increase PER1 gene expression in skin cells.

A specific example includes a botanical extract from *Echinacea purpurea* sold by Symrise under the brand name Symfinity™ 1298 which is an extract of *Echinacea purpurea* which is standardized during the extraction process to contain about 3% by weight of the total extract composition of cichoric acid. *Echinacea* extracts from different sources will vary in cichoric acid content, and as such will yield variable results in induction of PER1 gene expression. For example, we have observed that another component commonly found in extracts of *Echinacea*, specifically caftaric acid, does not increase PER1 gene expression in skin cells. Moreover, each species of *Echinacea* will differ in content of phenolic and cichoric acids. Ethanolic extract of the roots of *Echinacea purpura* will provide more cichoric acid than ethanolic extracts of *Echineacea angustifolia* or *Echinacea pallida*. The content of active ingredients in any extract is also very dependent on the method of extraction. For example, it is known that in many cases enzymatic browning during the extraction process will reduce the phenolic acid content of the resulting extract.

D. DNA Repair Enzymes

The composition used in the method of the invention may also contain one or more DNA repair enzymes. Suggested ranges are from about 0.00001 to about 35%, preferably from about 0.00005 to about 30%, more preferably from about 0.0001 to about 25% of one or more DNA repair enzymes.

DNA repair enzymes as disclosed in U.S. Pat. Nos. 5,077,211; 5,190,762; 5,272,079; and 5,296,231, all of which are hereby incorporated by reference in their entirety, are suitable for use in the compositions and method of the invention. One example of such a DNA repair enzyme may be purchased from AGI/Dermatics under the trade name Roxisomes®, and has the INCI name *Arabidopsis Thaliana* extract. It may be present alone or in admixture with lecithin and water. This DNA repair enzyme is known to be effective in repairing 8-oxo-Guanine base damage.

Another type of DNA repair enzyme that may be used is one that is known to be effective in repairing 06-methyl guanine base damage. It is sold by AGI/Dermatics under the tradename Adasomes®, and has the INCI name *Lactobacillus* ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of Micrococcus lysate (an end product of the controlled lysis of various species of micrococcus), lecithin, and water. Photosomes® comprise a mixture of plankton extract (which is the extract of marine biomass which includes one or more of the following organisms: thalassoplankton, green micro-algae, diatoms, greenish-blue and nitrogen-fixing seaweed), water, and lecithin.

Another type of DNA repair enzyme may be a component of various inactivated bacterial lysates such as *bifida* lysate or *bifida* ferment lysate, the latter a lysate from *bifido* bacteria which contains the metabolic products and cytoplasmic fractions when *bifido* bacteria are cultured, inactivated and then disintegrated. This material has the INCI name *bifida* Ferment Lysate.

Other suitable DNA repair enzymes include Endonuclease V, which may be produced by the denV gene of the bacteriophage T4. Also suitable are T4 endonuclease; $O^6$-methylguanine-DNA methyltransferases; photolyases such as uracil- and hypoxanthine-DNA glycosylases; apyrimidinic/apurinic endonucleases; DNA exonucleases, damaged-bases glycosylases (e.g., 3-methyladenine-DNA glycosylase); correndonucleases either alone or in complexes (e.g., *E. coli* uvrA/uvrB/uvrC endonuclease complex); APEX nuclease, which is a multi-functional DNA repair enzyme often referred to as "APE"; dihydrofolate reductase; terminal transferase; topoisomerase; $O^6$ benzyl guanine; DNA glycosylases.

Other types of suitable DNA repair enzymes may be categorized by the type of repair facilitated and include BER (base excision repair) or BER factor enzymes such as uracil-DNA glycosylase (UNG); single strand selective monofunctional uracil DNA glycosylase (SMUG1); 3,N(4)-ethenocytosine glycosylase (MBD4); thymine DNA-glycosylase (TDG); A/G-specific adenine DNA glycosylase (MUTYH); 8-oxoguanine DNA glycosylase (OGG1); endonuclease III-like (NTHL1); 3-methyladenine DNA glycosidase (MPG); DNA glycosylase/AP lyase (NEIL1 or 2); AP endonuclease (APEX 1 and 2), DNA ligase (LIG3), ligase accessory factor (XRCC1); DNA 5'-kinase/3'-phosphatase (PNKP); ADP-ribosyltransferase (PARP1 or 2).

Another category of DNA repair enzymes includes those that are believed to directly reverse damage such as $O^6$-MeG alkyl transferase (MGMT); 1-meA dioxygenase (ALKBH2 or ALKBH3).

Yet another category of enzymes operable to repair DNA/protein crosslinks includes Tyr-DNA phosphodiesterase (TDP1).

Also suitable are MMR (mismatch exision repair) DNA repair enzymes such as MutS protein homolog (MSH2); mismatch repair protein (MSH3); mutS homolog 4 (MSH4); MutS homolog 5 (MSH5); or G/T mismatch-binding protein (MSH6); DNA mismatch repair protein (PMS1, PMS2, MLH1, MLH3); Postmeiotic segregation increased 2-like protein (PMS2L3); or postmeiotic segregation increased 2-like 4 pseudogene (PMS2L4).

Also suitable are DNA repair enzymes are those known as nucleotide excision repair (NER) enzymes and include those such as Xeroderma pigmentosum group C-complementing protein (XPC); RAD23 (*S. cerevisiae*) homolog (RAD23B); caltractin isoform (CETN2); RFA Protein 1, 2, of 3 (RPA1, 2, or 3); 3' to 5' DNA helicase (ERCC3); 5' to 3' DNA helicase (ERCC2); basic transcription factor (GTF2H1, GTF2H2, GTF2H3, GTF2H4, GTF2H5); CDK activating kinase (CDK7, CCNH); cyclin G1-interacting protein (MNAT1); DNA excision repair protein ERCC-51; excision repair cross-complementing 1 (ERCC1); DNA ligase 1 (LIG1); ATP-dependent helicase (ERCC6); and the like.

Also suitable may be DNA repair enzymes in the category that facilitate homologous recombination and include, but are not limited to DNA repair protein RAD51 homolog (RAD51, RAD51L1, RAD51B etc.); DNA repair protein XRCC2; DNA repair protein XRCC3; DNA repair protein RAD52; ATPase (RAD50); 3' exonuclease (MRE11A); and so on.

DNA repair enzymes that are DNA polymerases are also suitable and include DNA polymerase beta subunit (POLB); DNA polymerase gamma (POLG); DNA polymerase subunit delta (POLD1); DNA polymerase II subunit A (POLE); DNA polymerase delta auxiliary protein (PCNA); DNA polymerase zeta (POLZ); MAD2 homolog ((REV7); DNA polymerase eta (POLH): DNA polymerase kappa (POLK): and the like.

Various types of DNA repair enzymes that are often referred to as "editing and processing nucleases" include 3'-nuclease; 3'-exonuclease; 5'-exonuclease; endonuclease; and the like.

Other examples of DNA repair enzymes include DNA helicases including such as ATP DNA helicase and so on.

The DNA repair enzymes may be present as components of botanical extracts, bacterial lysates, biological materials, and the like. For example, botanical extracts may contain DNA repair enzymes.

E. Humectants

The composition may contain one or more humectants. If present, they may range from about 0.01 to 75%, preferably from about 0.5 to 70%, more preferably from about 0.5 to 40%. Examples of suitable humectants include glycols, sugars, and the like. Suitable glycols are in monomeric or polymeric form and include polyethylene and polypropylene glycols such as PEG 4-10, which are polyethylene glycols having from 4 to 10 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

F. Surfactants

It may be desirable for the composition to contain one more surfactants, especially if in the emulsion form. However, such surfactants may be used if the compositions are solutions, suspensions, or anhydrous also, and will assist in dispersing ingredients that have polarity, for example pigments. Such surfactants may be silicone or organic based. The surfactants will also aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

1. Organic Nonionic Surfactants

The composition may comprise one or more nonionic organic surfactants. Suitable nonionic surfactants include alkoxylated alcohols or ethers, formed by the reaction of an alcohol with an alkylene oxide, usually ethylene or propylene oxide. Suitable alcohols include mono-, di-, or polyhydric short chain (C1-6) alcohols; aromatic or aliphatic saturated or unsaturated fatty (C12-40) alcohols, of cholesterol; and so on.

In one embodiment the alcohol is cholesterol, or an aromatic or aliphatic saturated or unsaturated fatty alcohol which may have from 6 to 40, preferably from about 10 to 30, more preferably from about 12 to 22 carbon atoms. Examples include oleyl alcohol, cetearyl alcohol, cetyl alcohol, stearyl alcohol, isostearyl alcohol, behenyl alcohol, and the like. Examples of such ingredients include Oleth 2-100; Steareth 2-100; Beheneth 5-30; Ceteareth 2-100; Ceteth 2-100; Choleth 2-100 wherein the number range means the number of repeating ethylene oxide units, e.g. Ceteth 2-100 means Ceteth where the number of repeating ethylene oxide units ranges from 2 to 100. Derivatives of alkoxylated alcohols are also suitable, such as phosphoric acid esters thereof.

Some preferred organic nonionic surfactants include Oleth-3, Oleth-5, Oleth-3 phosphate, Choleth-24; Ceteth-24; and so on.

Also suitable are alkoxylated alcohols formed with mono-, di-, or polyhydric short chain alcohols, for example those having from about 1 to 6 carbon atoms. Examples include glucose, glycerin, or alkylated derivatives thereof. Examples include glycereth 2-100; gluceth 2-100; methyl gluceth 2-100 and so on. More preferred are methyl gluceth-20; glycereth-26 and the like.

Other types of alkoxylated alcohols are suitable surfactants, including ethylene oxide polymers having varying numbers of repeating EO groups, generally referred to as PEG 12 to 200. More preferred are PEG-75, which is may be purchased from Dow Chemical under the trade name Carbowax PEG-3350.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

2. Silicone or Silane Surfactants

Also suitable are various types of silicone or silane-based surfactants. Examples include organosiloxanes substituted with ethylene oxide or propylene oxide groups such as PEG dimethicones which are dimethicones substituted with polyethylene glycols including those having the INCI names PEG-1 dimethicone; PEG-4 dimethicone; PEG-8 dimethicone; PEG-12 dimethicone; PEG-20 dimethicone; and so on.

Also suitable are silanes substituted with ethoxy groups or propoxy groups or both, such as various types of PEG methyl ether silanes such as bis-PEG-18 methyl ether dimethyl silane; and so on.

Further examples of silicone based surfactants include those having the generic names dimethicone copolyol; cetyl dimethicone copolyol; and so on.

G. Botanical Extracts

It may be desirable to incorporate one more additional botanical extracts into the composition. If present suggested ranges are from about 0.0001 to 20%, preferably from about 0.0005 to 15%, more preferably from about 0.001 to 10%. Suitable botanical extracts include extracts from plants (herbs, roots, flowers, fruits, seeds) such as flowers, fruits, vegetables, and so on, including yeast ferment extract, *Padina pavonica* extract, *Thermus thermophilis* ferment extract, *Camelina sativa* seed oil, *Boswellia serrata* extract, olive extract, *Acacia dalbata* extract, *Acer saccharinum* (sugar maple), *Acidopholus, Acorus, Aesculus, Agaricus, Agave, Agrimonia*, algae, aloe, citrus, *Brassica*, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza flabra, Salix nigra, Macrocycstis pyrifera, Pyrus nalus, Saxifraga sarmentosa, Vitis vinifera, Morus nigra, Scutellaria baicalensis, Anthemis nobilis, Salvia sclarea, Rosmarinus officianalis, Citrus Medica limonum, Panax ginseng, Siegesbeckia orientalis, Fructus mume, Ascophyllum nodosum, Glycine soja* extract, *Beta vulgaris, Haberlea rhodopensis, Polygonum cuspidatum, Citrus Aurantium dulcis, Vitis vinifera, Selaginella tamariscina, Humulus lupulus, Citrus reticulata* Peel, *Punica granatum, Asparagopsis, Curcuma longa, Menyanthes trifoliata, Helianthus annuus*, Hordeum Vulgare, *Cucumis sativus, Evernia prunastri, Evernia furfuracea, Kola Acuminata*, and mixtures thereof. If desired such botanical extracts may be fermented to increase potency or activity. Fermentation may be accomplished by standard fermentation techniques using bacteria or yeast.

H. Biological Materials

Also suitable are various types of biological materials such as those derived from cells, fermented materials, and so on. If present such materials may range from about 0.001 to 30%, preferably from about 0.005 to 25%, more preferably from about 0.01 to 20%. Examples include fragments of cellular RNA or DNA, probiotic microorganisms, or ferments of microorganisms and organic materials from plants such as leaves, seeds, extracts, flowers, etc. Particularly preferred are RNA fragments.

I. Oils

In the event the compositions of the invention are in emulsion form, the composition will comprise an oil phase. Oily ingredients are desirable for the skin moisturizing and protective properties. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C. If present, such oils may range from about 0.01 to 85%, preferably from about 0.05 to 80%, more preferably from about 0.1 to 50%.

Suitable volatile oils generally have a viscosity ranging from about 0.5 to 5 centistokes 25° C. and include linear silicones, cyclic silicones, paraffinic hydrocarbons, or mixtures thereof.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone which may be purchased from Shin-Etsu Silicones under the tradename TMF-1.5, having a viscosity of 1.5 centistokes at 25° C.

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to mono-, di-, and triesters.

Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Suitable triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters".

It may be desirable to incorporate one or more nonvolatile hydrocarbon oils into the composition such as $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diisostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone as well as dimethicones, phenyl substituted dimethicones and the like.

J. Vitamins and Antioxidants

It may be desirable to incorporate one or more vitamins or antioxidants in the compositions. If present, suggested ranges are from about 0.001 to 20%, preferably from about 0.005 to 15%, more preferably from about 0.010 to 10%. Preferably such vitamins, vitamin derivatives and/or antioxidants are operable to scavenge free radicals in the form of singlet oxygen. Such vitamins may include tocopherol or its derivatives such as tocopherol acetate, tocopherol ferulate; ascorbic acid or its derivatives such as ascorbyl palmitate, magnesium ascorbyl phosphate; Vitamin A or its derivatives such as retinyl palmitate; or vitamins D, K, B, or derivatives thereof.

K. Preferred Compositions

Preferred compositions are in the aqueous solution or emulsion form and contain at least one Polymer, at least one HMW HA, at least one LMW HA, at least on polyamino acid, water, and an ingredient selected from the group consisting of (1) proteasome activator, (2) autophagy activator, (3) CLOCK or PER1 gene activator. (4) DNA repair enzyme; and (5) mixtures thereof.

A most preferred composition comprises an aqueous solution or emulsion containing at least one Polymer, at least one HMW HA, at least one LMW HA, at least on polyamino acid, water, inactivated bacterial lysates of *bifido* bacterium, and ingredient selected from the group consisting of (1) proteasome activator, (2) autophagy activator, (3) CLOCK or PER1 gene activator. (4) DNA repair enzyme; and (5) mixtures thereof.

The invention will be further described in connection with the following examples which are set forth for the purposes of illustration only.

Example 1

A composition (Composition 1) that formed a micro-mesh hydrogel was prepared as follows:

| Ingredient | | Concentration |
|---|---|---|
| Trade Name | INCI Name | (Wt %) |
| Sepimax Zen | Polyacrylate Crosspolymer-6 | 0.1 |
| Hyaluronic Acid, Sodium Salt | Sodium Hyaluronate (HMW) | 0.11 |
| Hyactive 10 | Sodium Hyaluronate (LMW) | 0.05 |
| Aquadew SPA-30B | Sodium Polyaspartate | 0.5 |

-continued

| Ingredient | | Concentration |
|---|---|---|
| Trade Name | INCI Name | (Wt %) |
| Phenoxetol | Phenoxyethanol | 0.5 |
| | Water | q.s. 100 |

The composition was prepared by combining phenoxyethanol and water and mixing well. The HMW HA was added to the mixture and mixed well till uniform. The LMW HA was added to the mixture and mixed well till uniform. Polyacrylate crosspolymer-6 was then added and mixed well till uniform. Sodium polyaspartate was added last and the mixture mixed well till uniform.

Figure 1B:
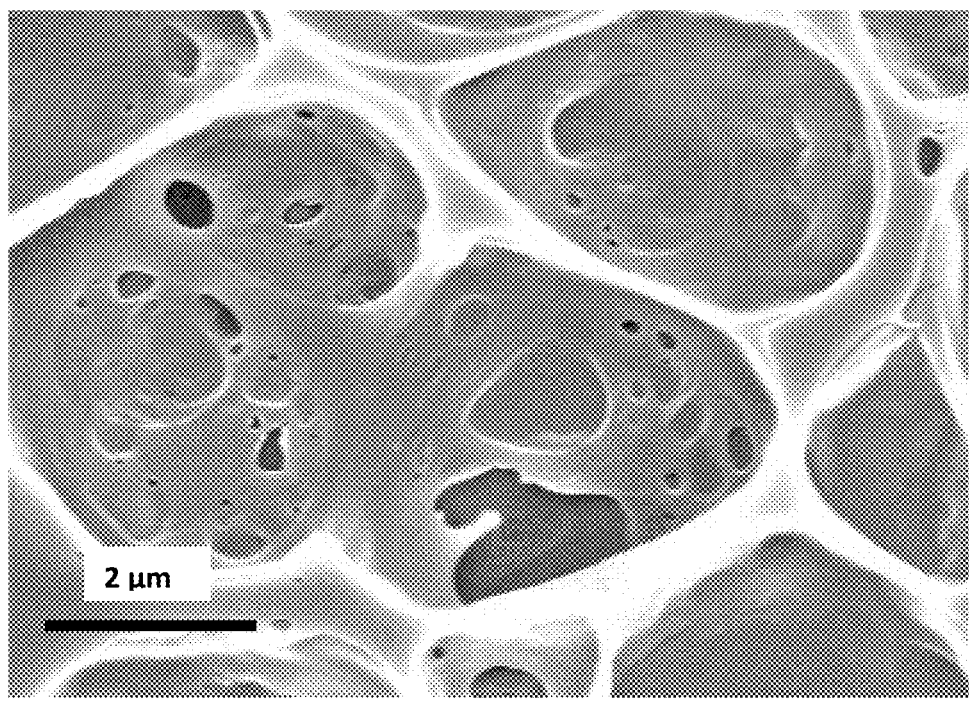
FIG. 1B: shows a SEM image of the Micro-Mesh hydrogel made in Example 1 for a closer view of the Micro-Mesh structure.
Figure 2A:
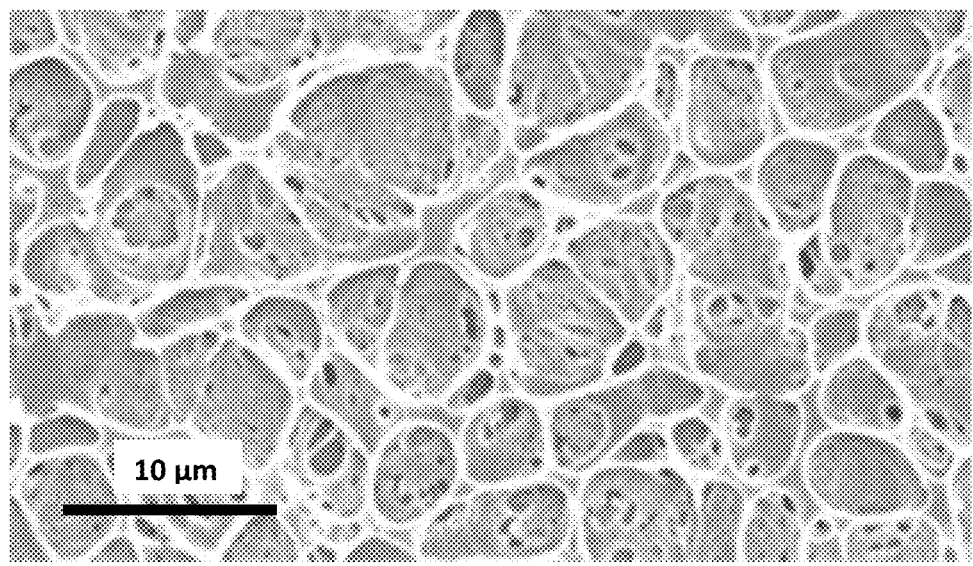
FIG. 2A: shows a SEM image of Composition 2 made in Example 2.
Figure 2B:
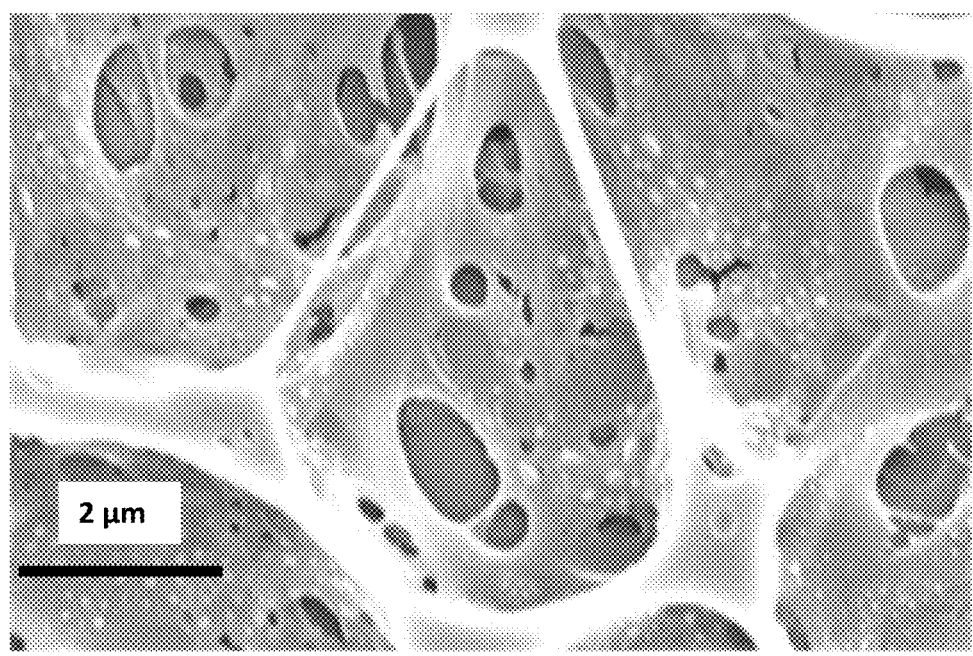
FIG. 2B: shows a SEM image of Composition 2 made in Example 2 for a closer view of its structure.
Figure 3A:
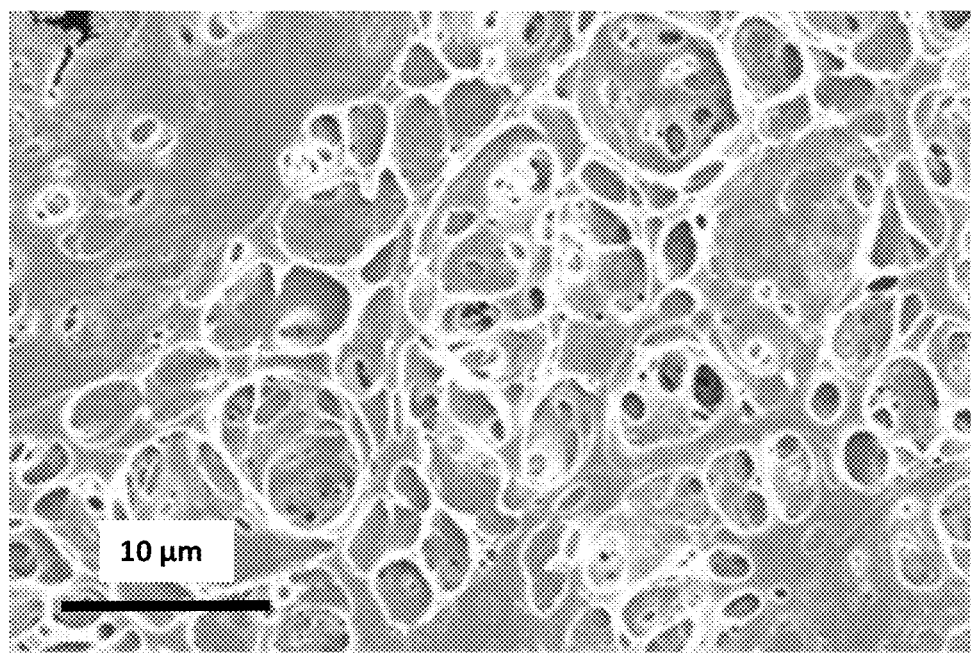
FIG. 3A: shows a SEM image of Composition 3 made in Example 2.
Figure 3B:
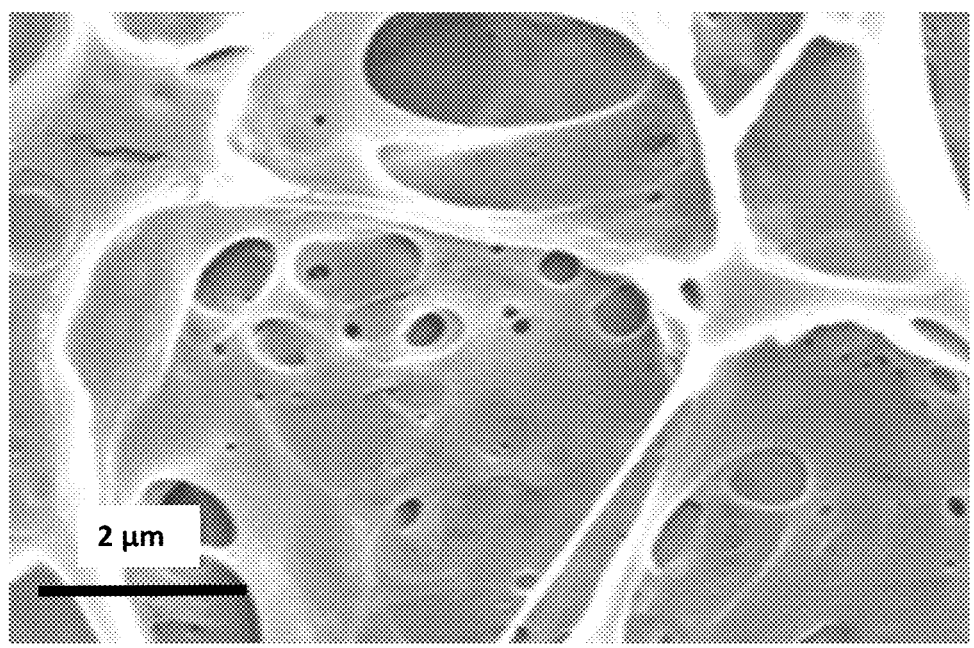
FIG. 3B: shows a SEM image of Composition 3 made in Example 2 for a closer view of its structure.
Figure 4A:
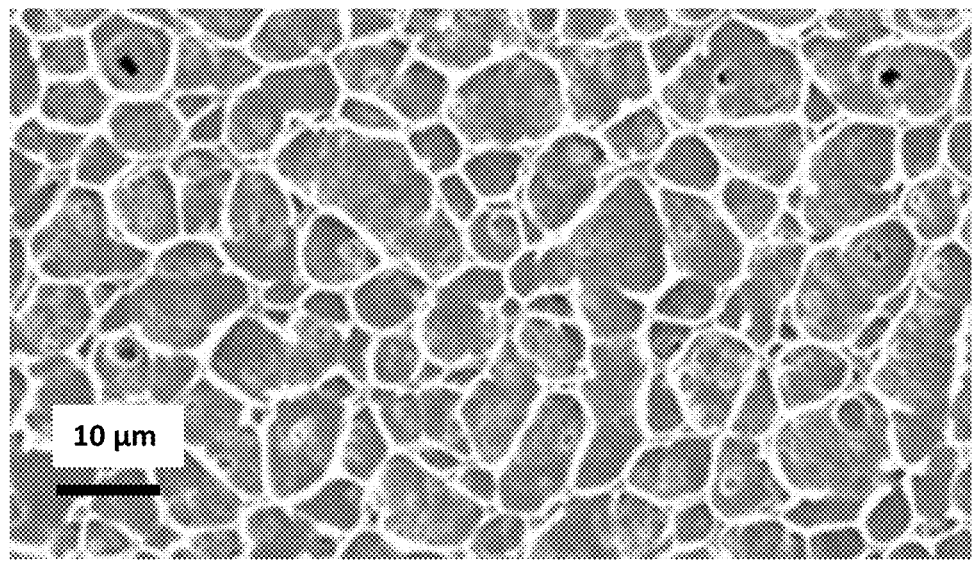
FIG. 4A: shows a SEM image of Composition 4 made in Example 2.
Figure 4B:
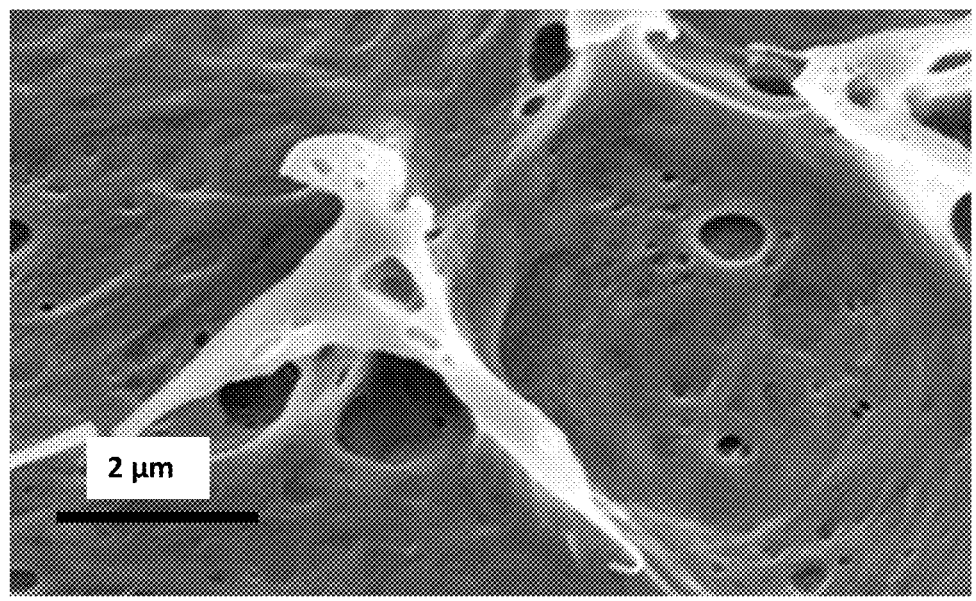
FIG. 4B: shows a SEM image of Composition 4 made in Example 2 for a closer view of its structure.
Figure 5A:
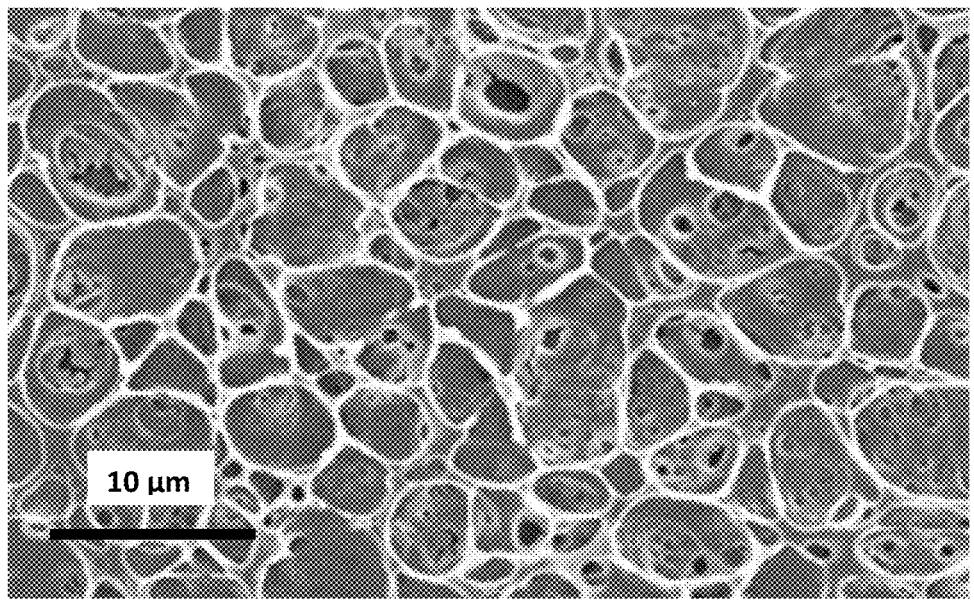
FIG. 5A: shows a SEM image of Composition 5 made in Example 2.
Figure 5B:
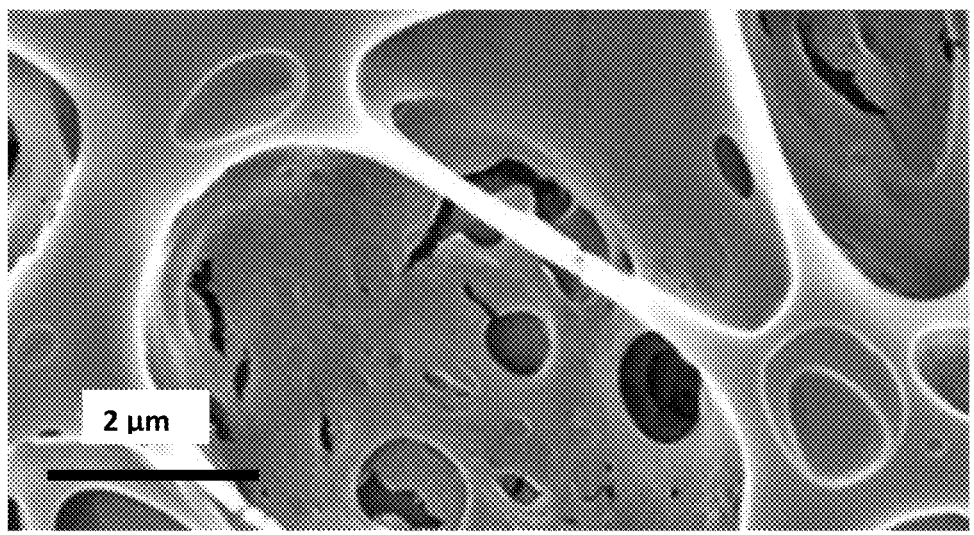
FIG. 5B: shows a SEM image of Composition 5 made in Example 2 for a closer view of its structure.
Figure 6A:
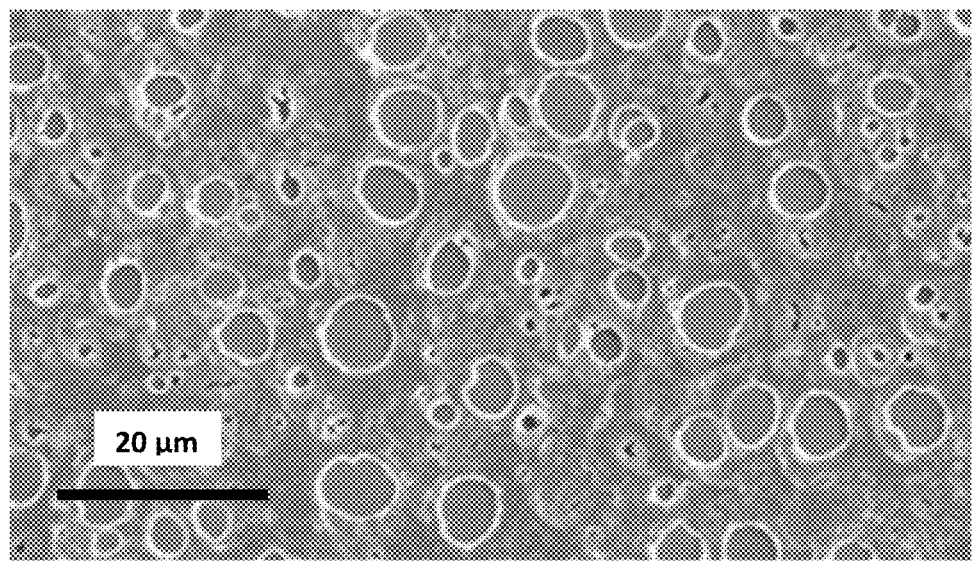
FIG. 6A: shows a SEM image of Composition 6 made in Example 2.
Figure 6B:
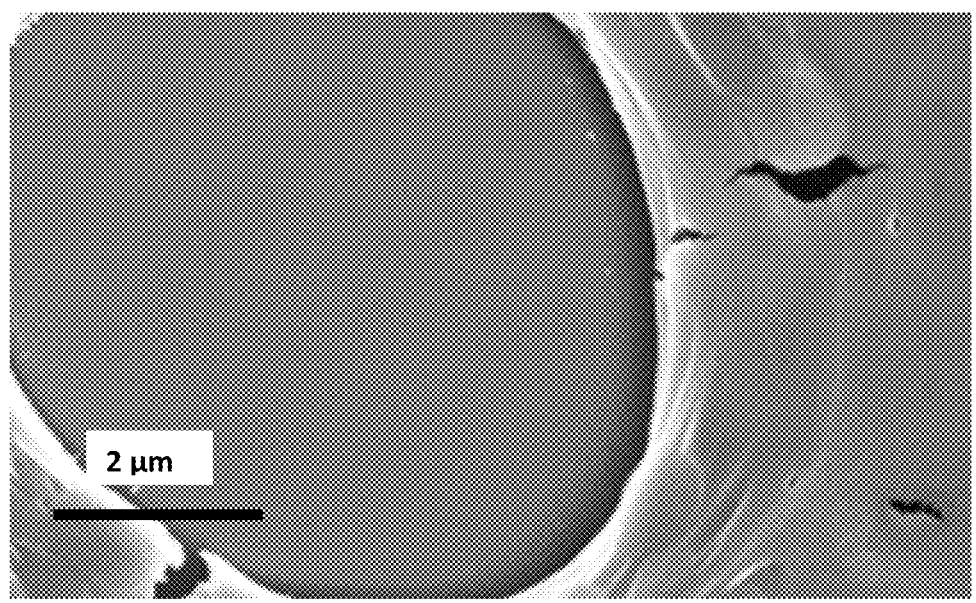
FIG. 6B: shows a SEM image of Composition 6 made in Example 2 for a closer view of its structure.
Figure 7A:
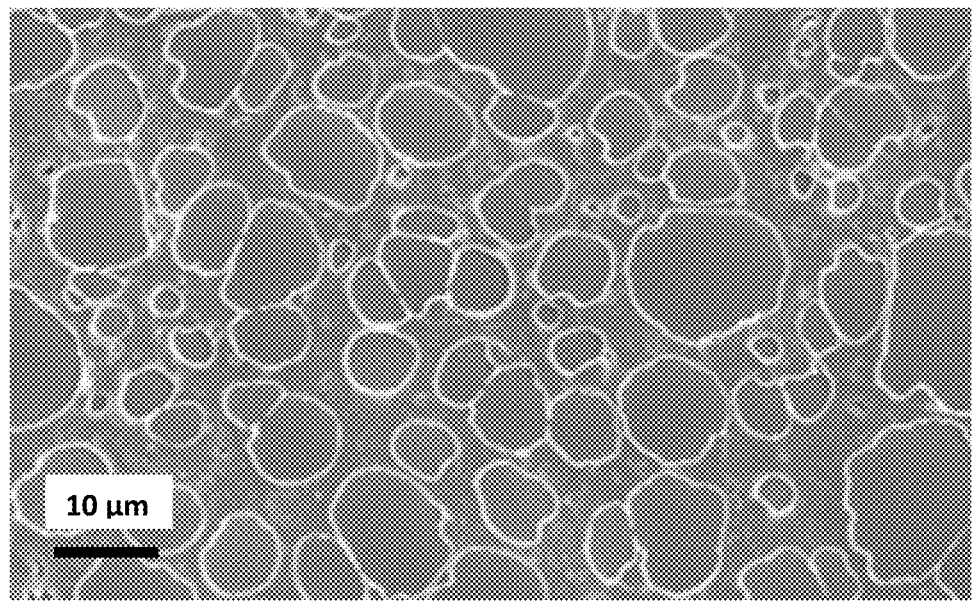
FIG. 7A: shows a SEM image of Composition 7 made in Example 2.
Figure 7B:
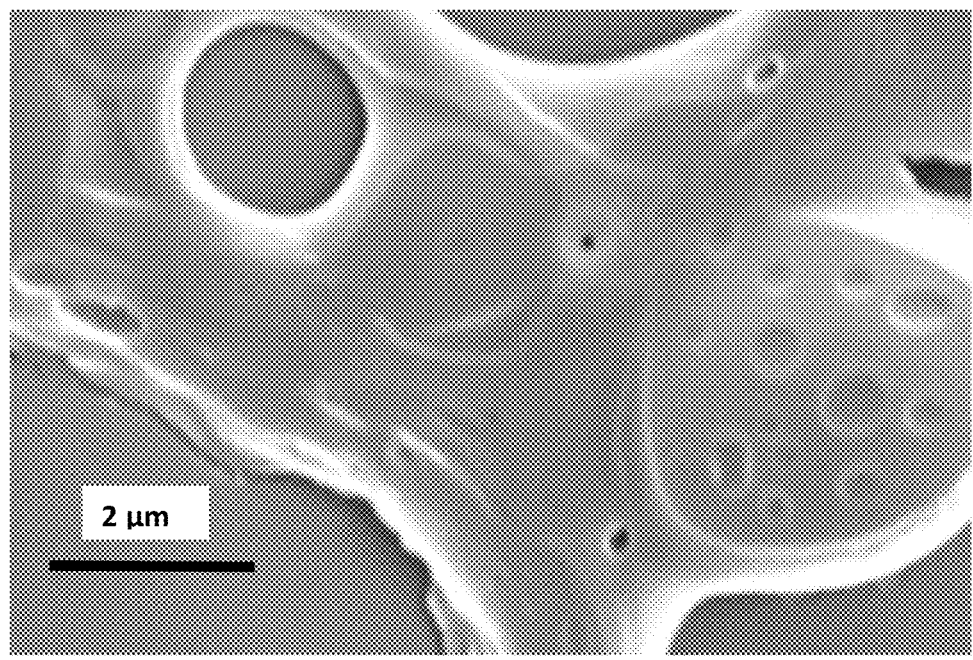
FIG. 7B: shows a SEM image of Composition 7 made in Example 2 for a closer view of its structure.
Figure 8A:
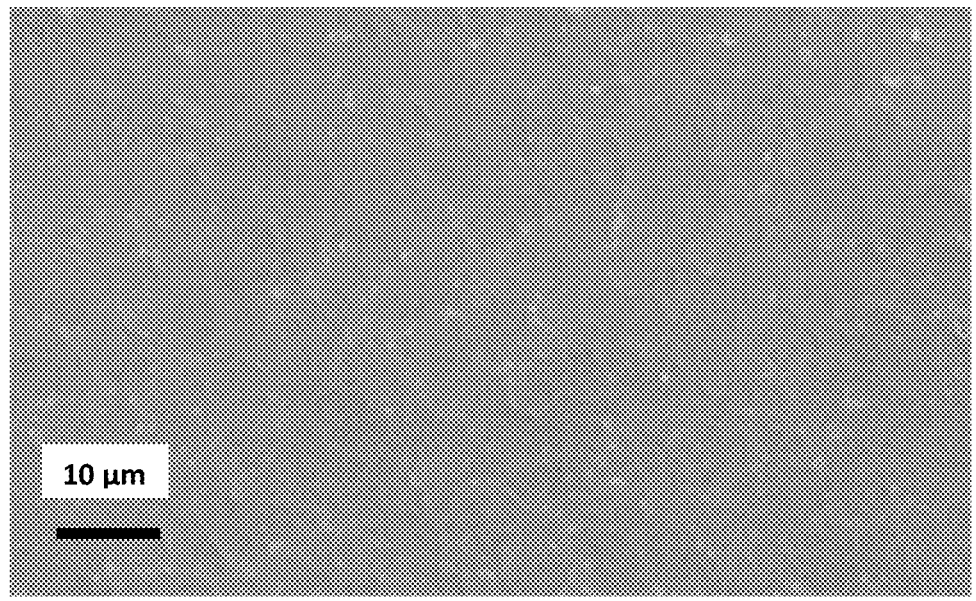
FIG. 8A: shows a SEM image of Composition 8 made in Example 2.
Figure 8B:
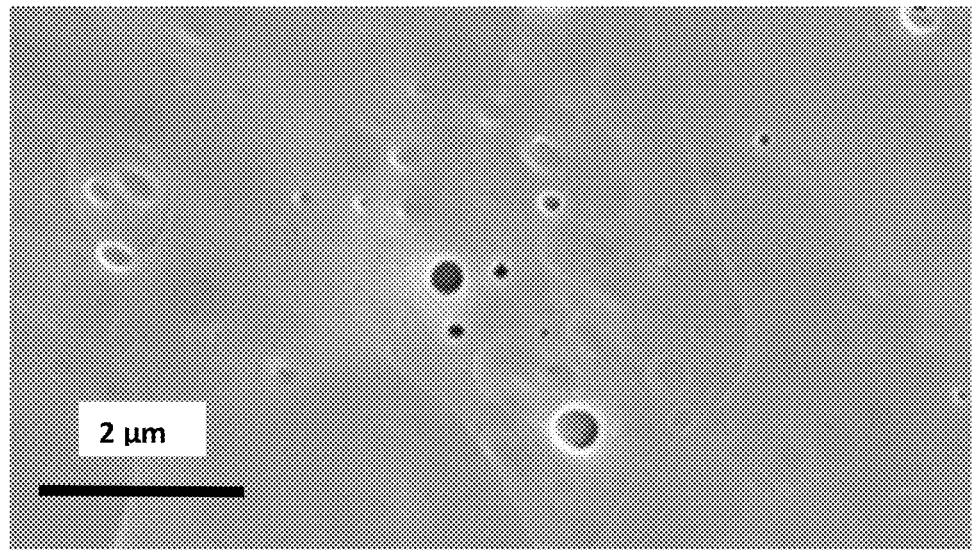
FIG. 8B: shows a SEM image of Composition 8 made in Example 2 for a closer view of its structure.
Figure 9A:
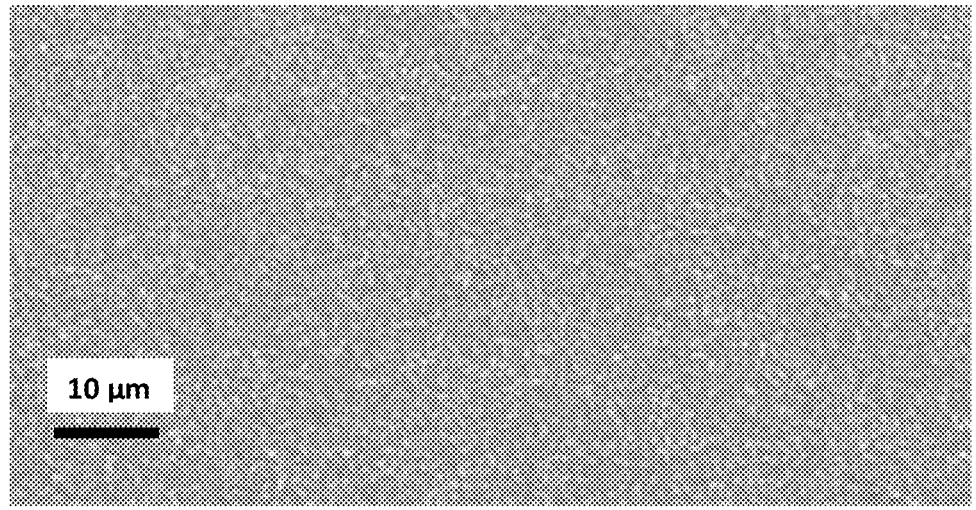
FIG. 9A: shows a SEM image of Composition 9 made in Example 2.
Figure 9B:
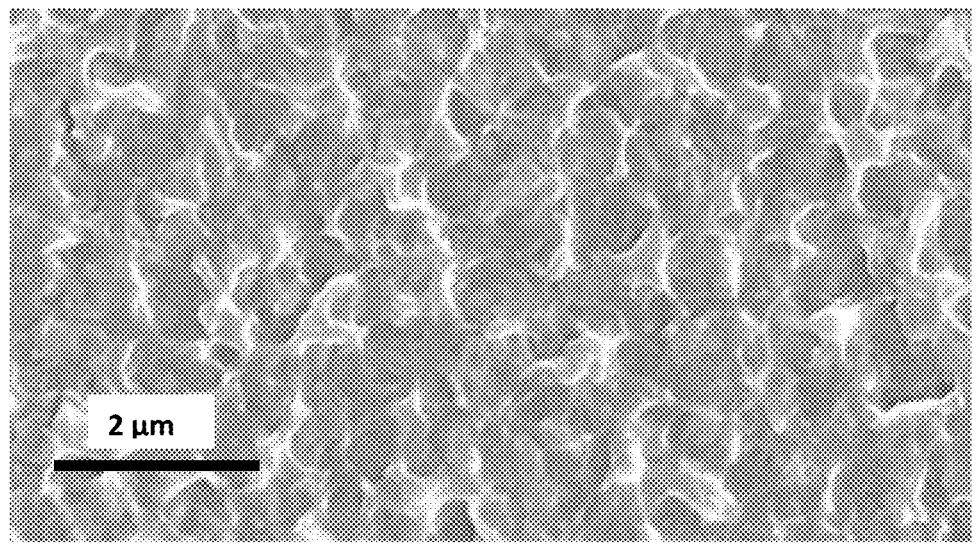
FIG. 9B: shows a SEM image of Composition 9 made in Example 2 for a closer view of its structure.
Figure 10A:
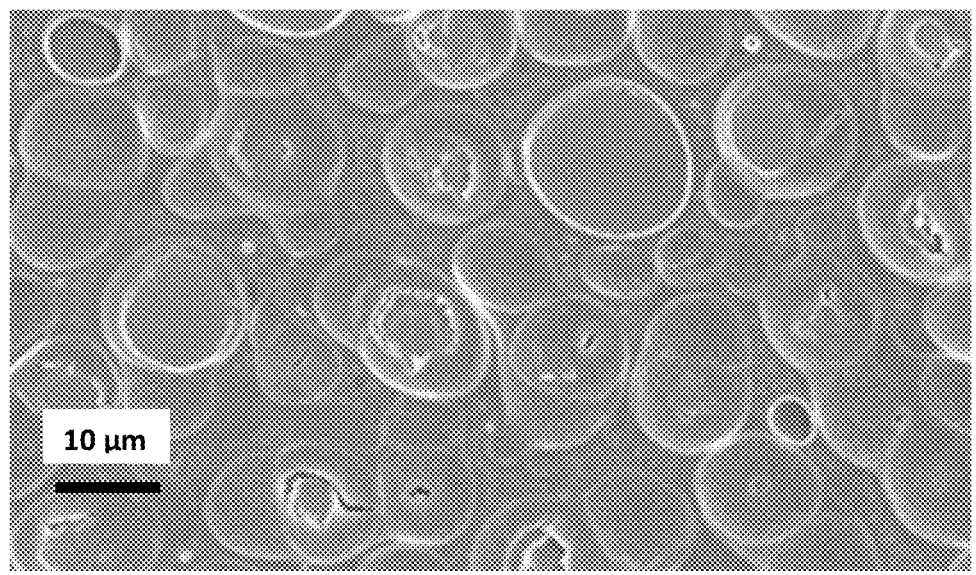
FIG. 10A: shows a SEM image of Composition 10 made in Example 2.
Figure 10B:
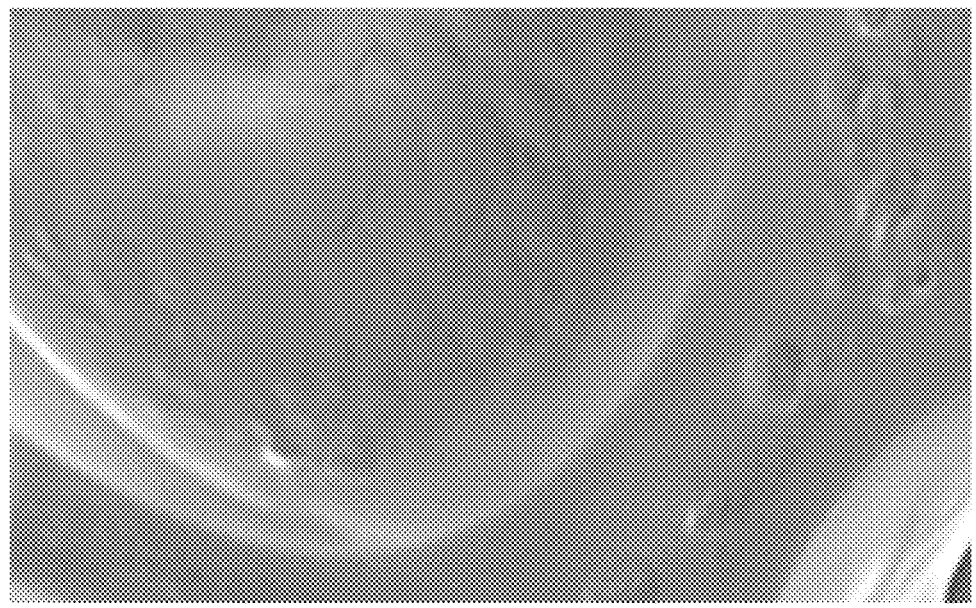
FIG. 10B: shows a SEM image of Composition 10 made in Example 2 for a closer view of its structure.
Figure 11A:
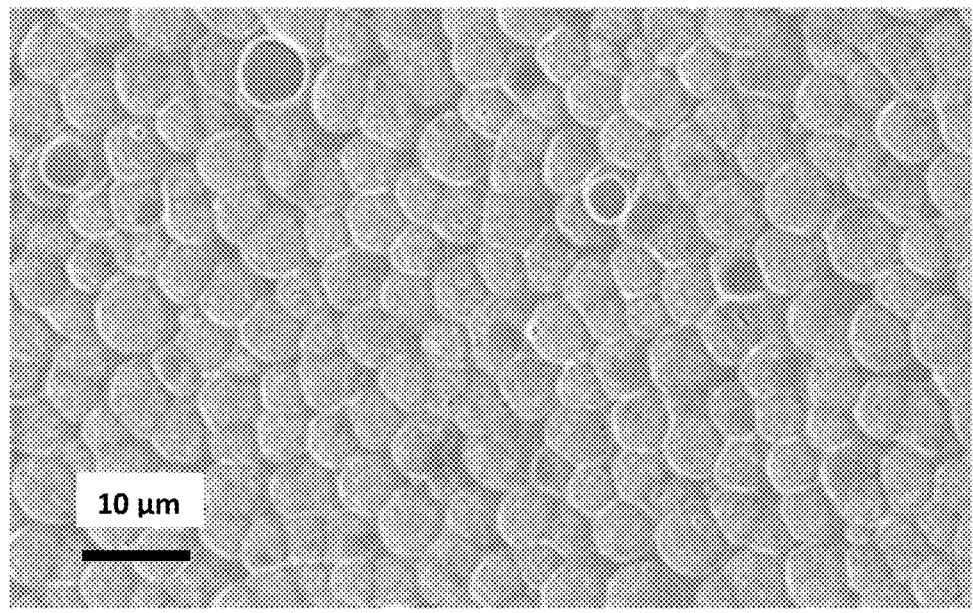
FIG. 11A: shows a SEM image of Composition 11 made in Example 2.
Figure 11B:
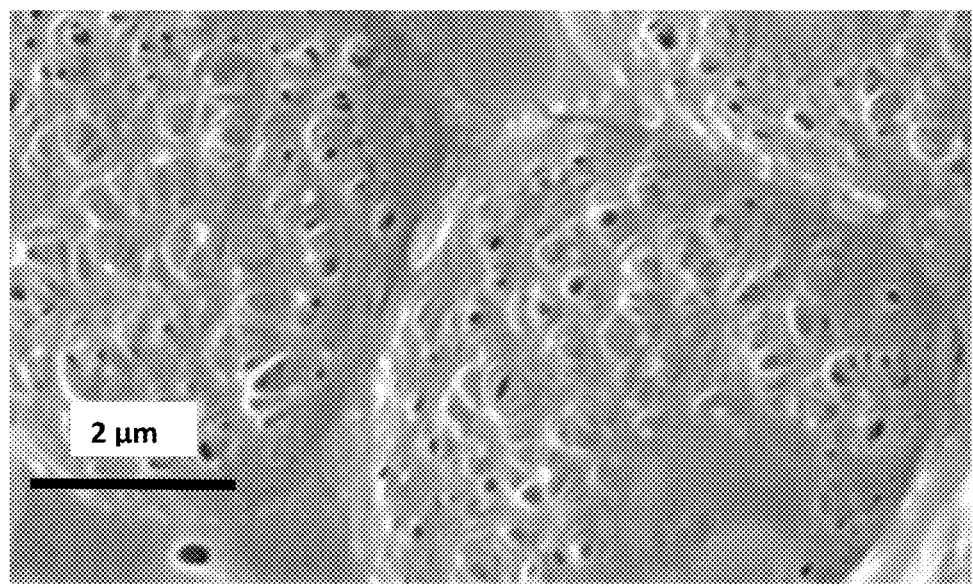
FIG. 11B: shows a SEM image of Composition 11 made in Example 2 for a closer view of its structure.
Figure 12:
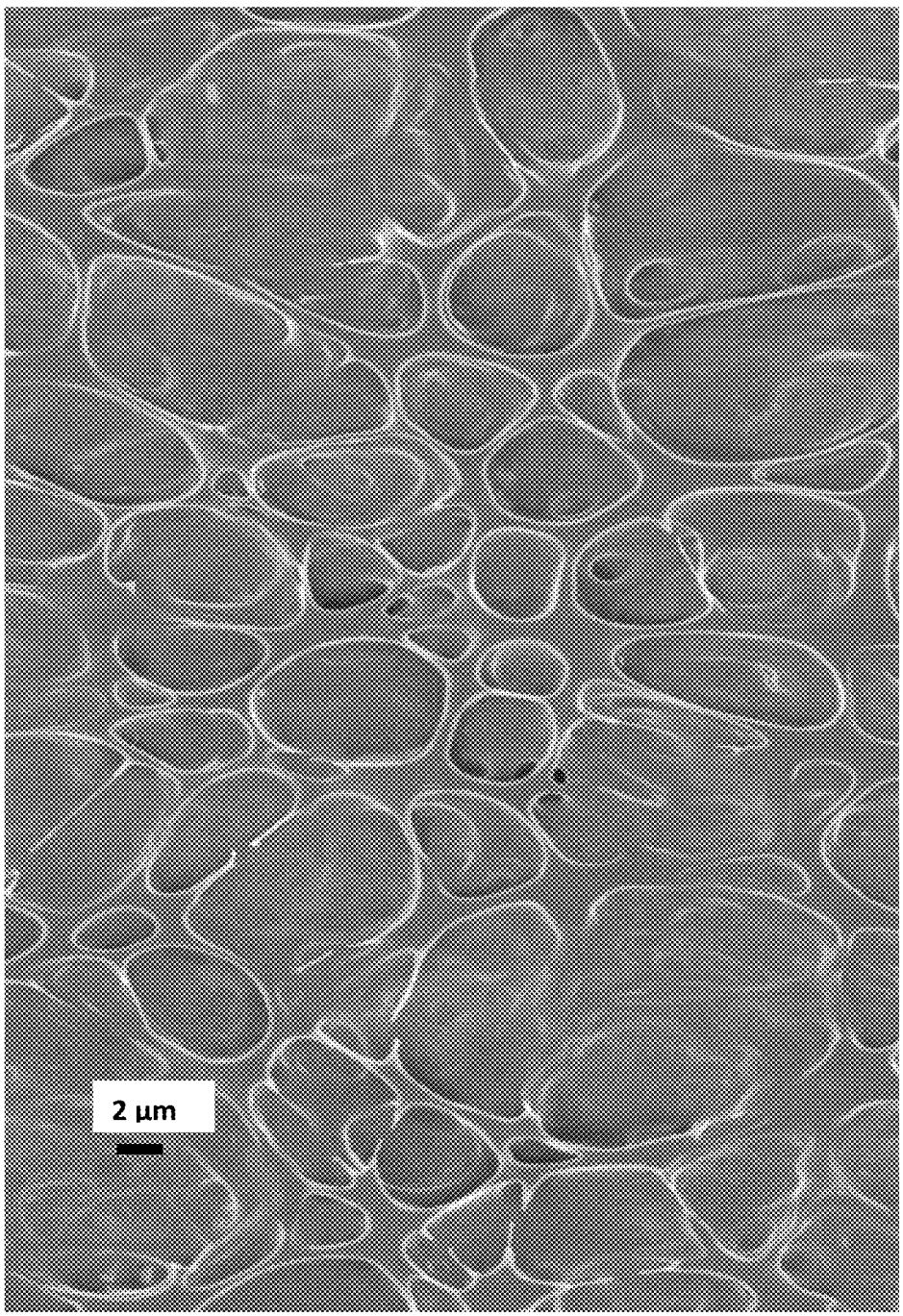
FIG. 12: shows a SEM image of Composition 12 made in Example 3.
Figure 13:
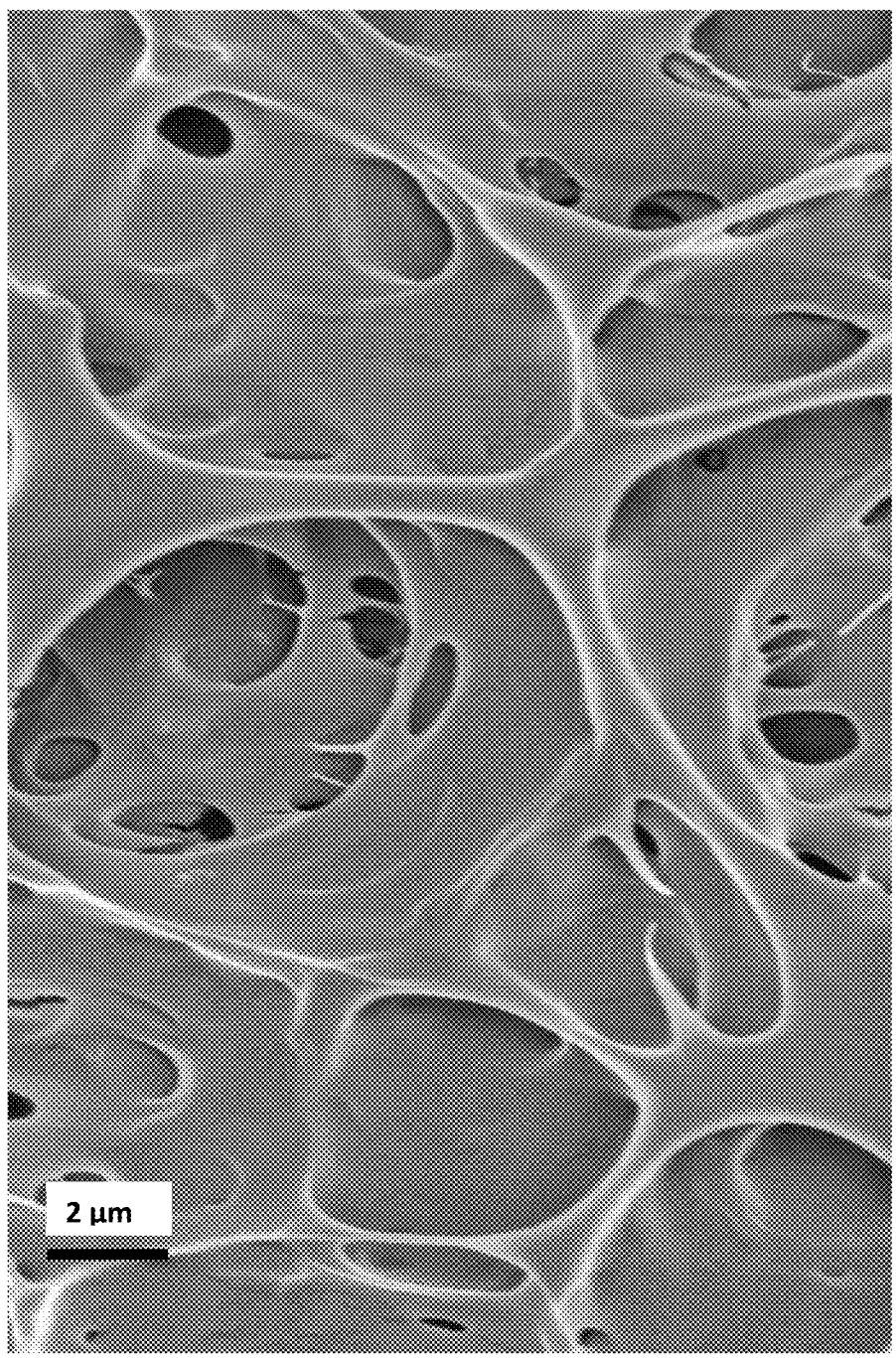
FIG. 13: shows a SEM image of Composition 13 made in Example 3.
Figure 14:
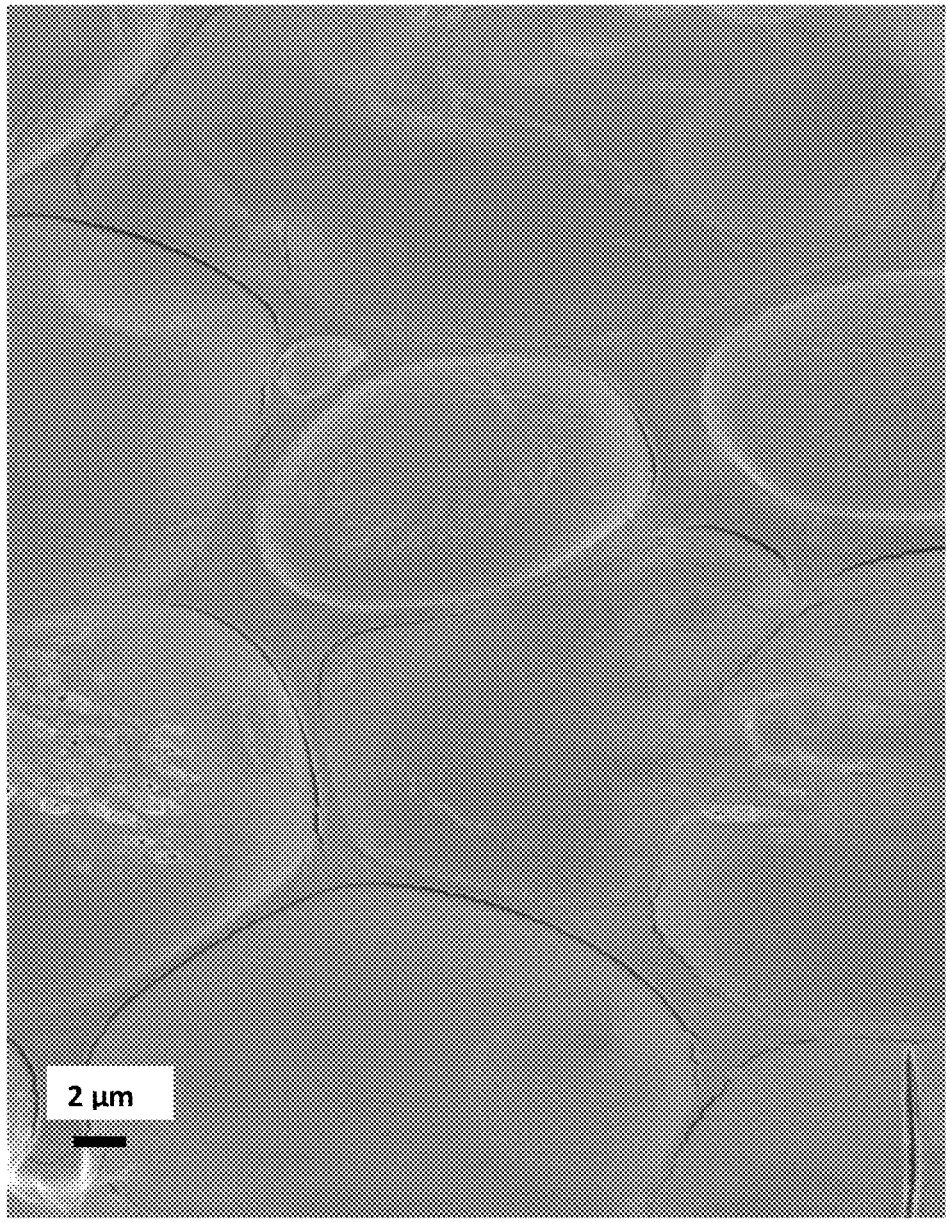
FIG. 14: shows a SEM image of Composition 14 made in Example 3.
Figure 15:
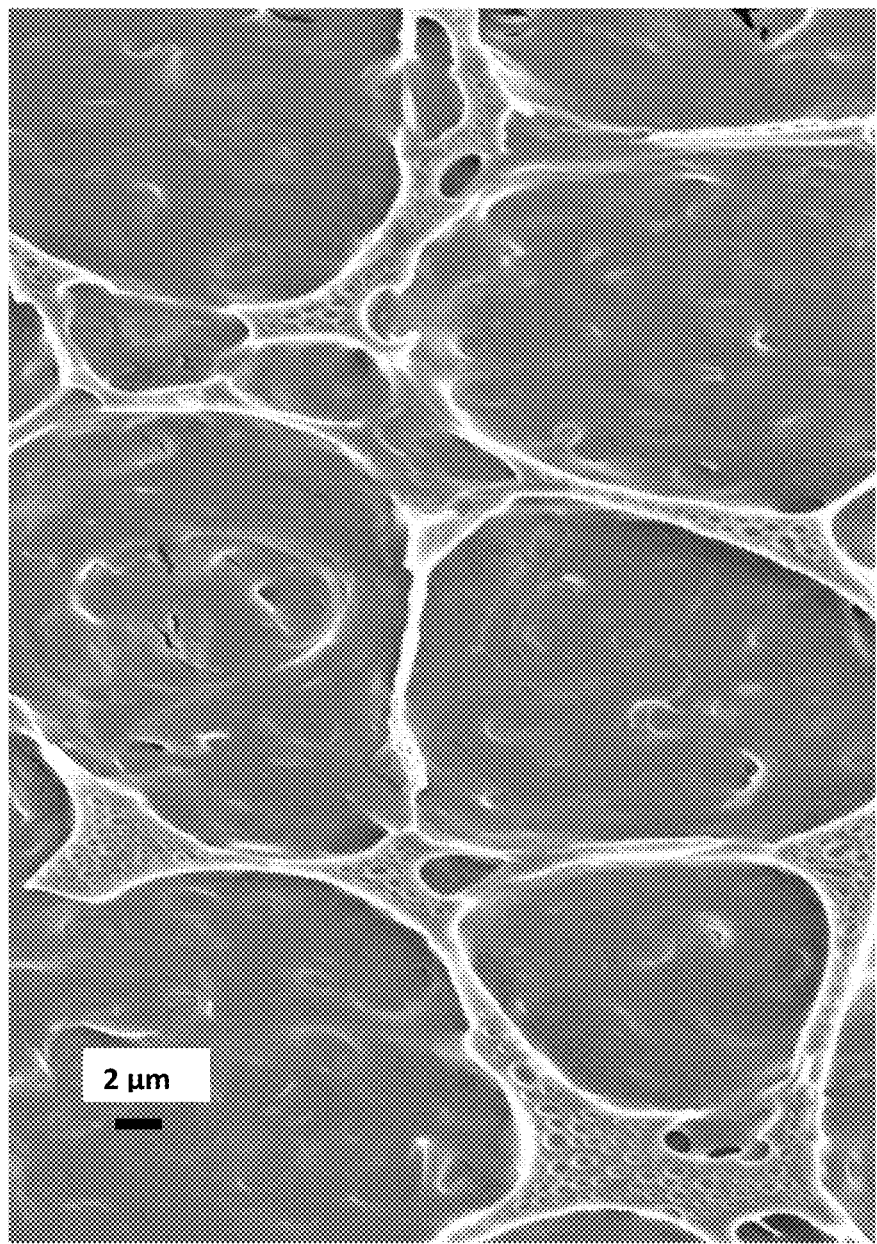
FIG. 15: shows a SEM image of Composition 15 made in Example 3.
Figure 16:
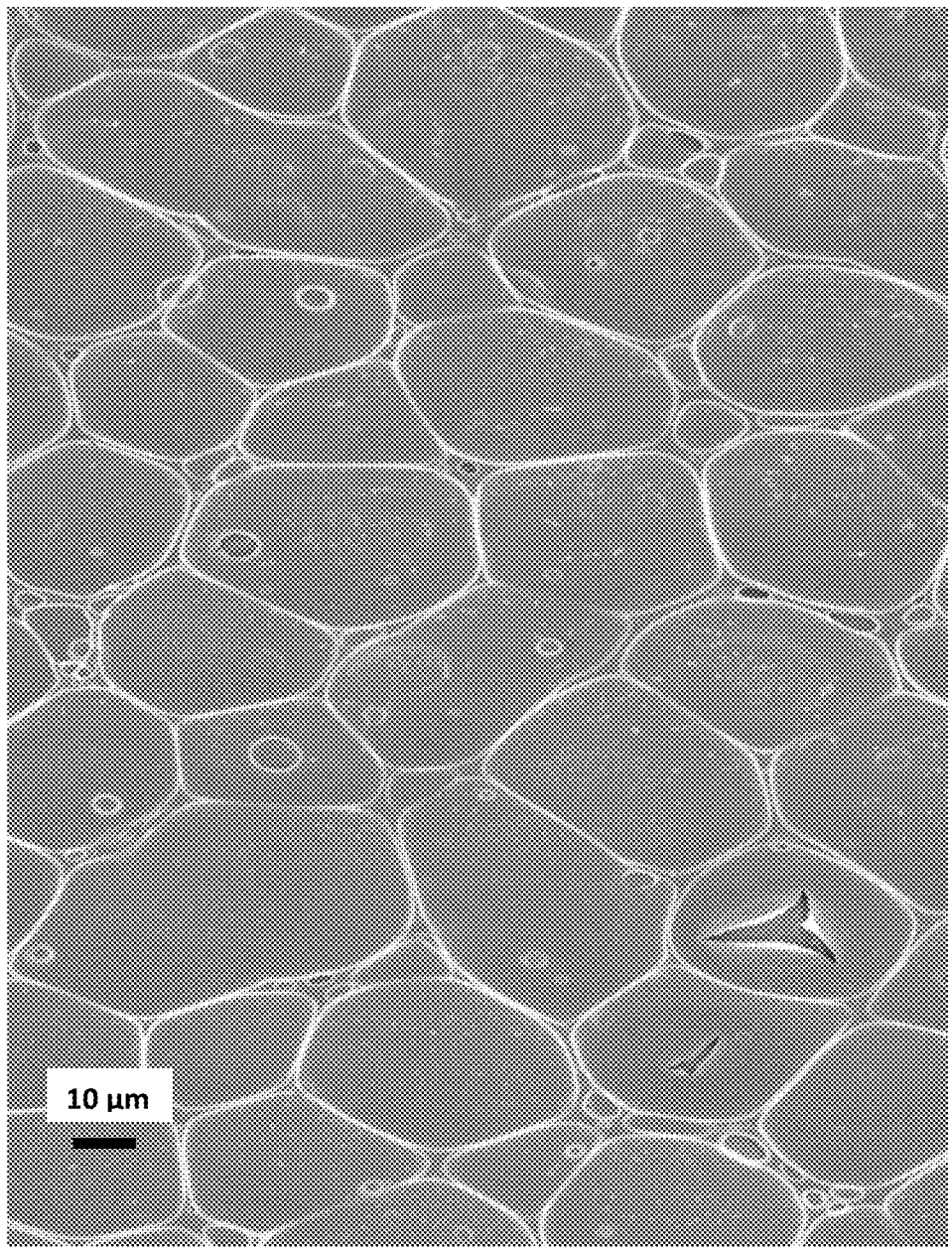
FIG. 16: shows a SEM image of Composition 16 made in Example 3.
Figure 17:
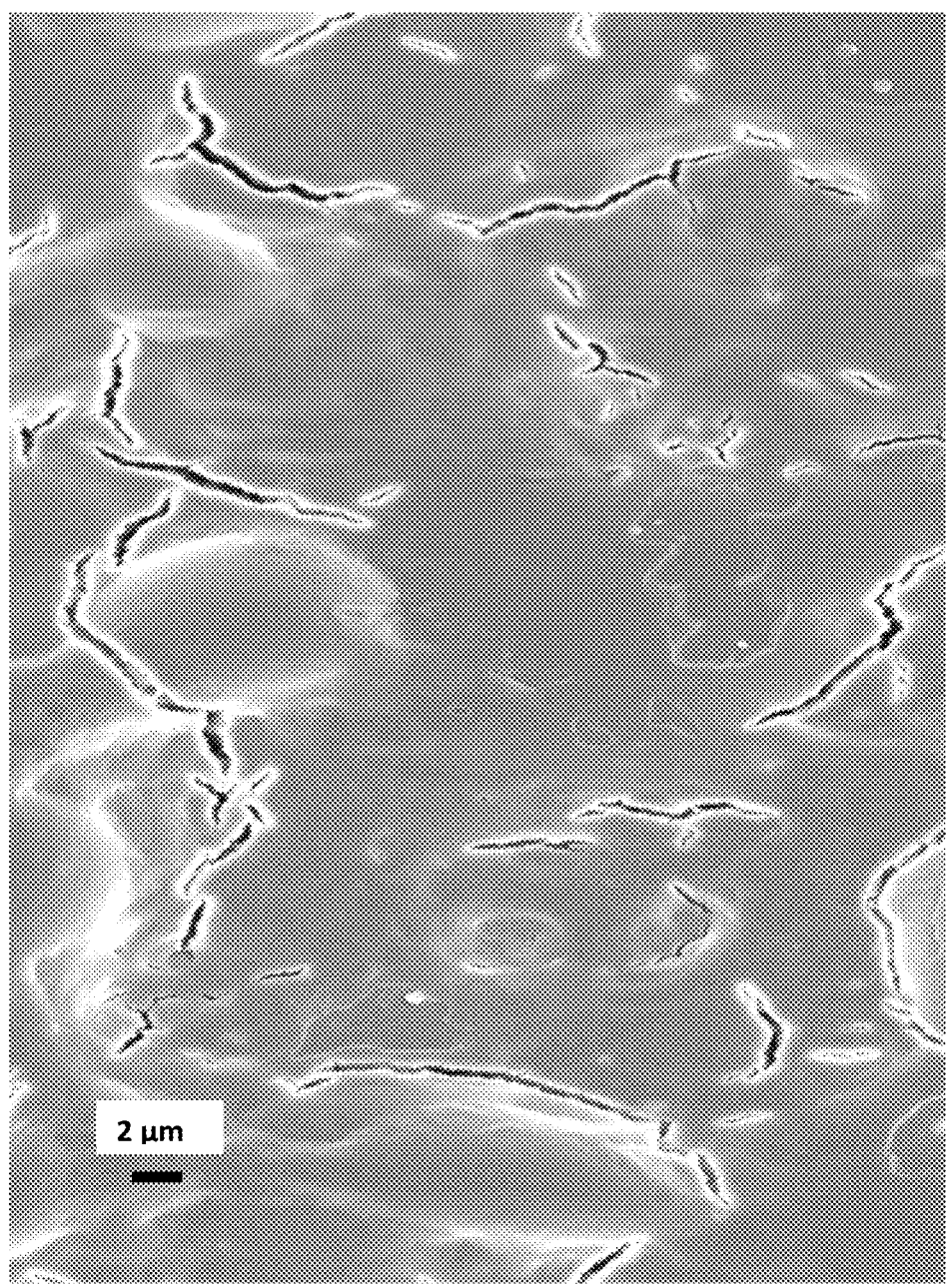
FIG. 17: shows a SEM image of Composition 17 made in Example 3.
Figure 18A:
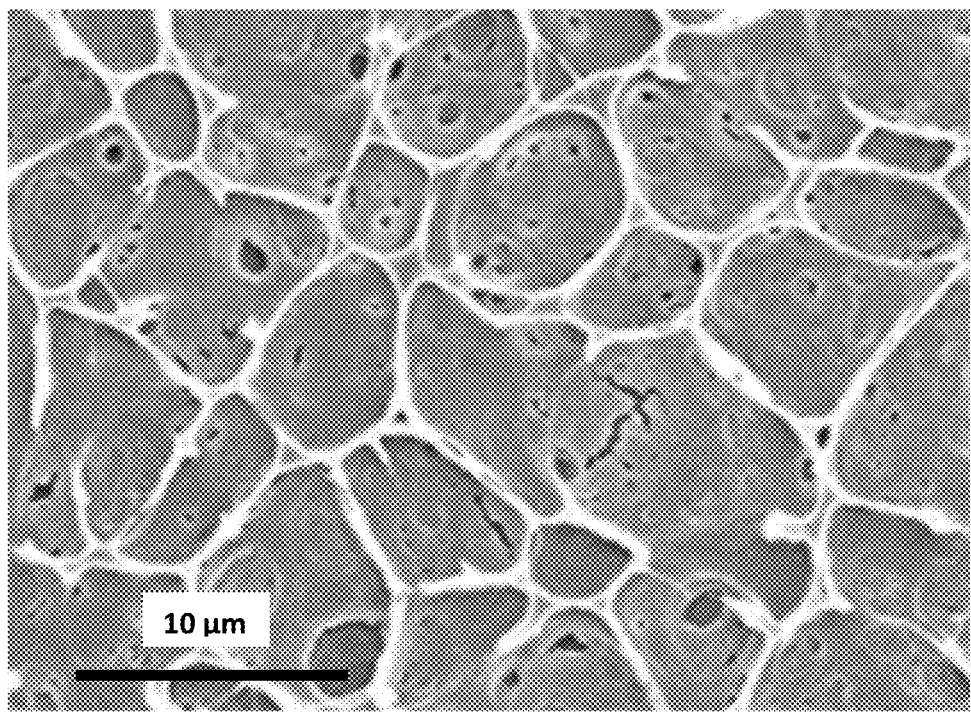
FIG. 18A: shows a SEM image of Composition 18 made in Example 4.
Figure 18B:
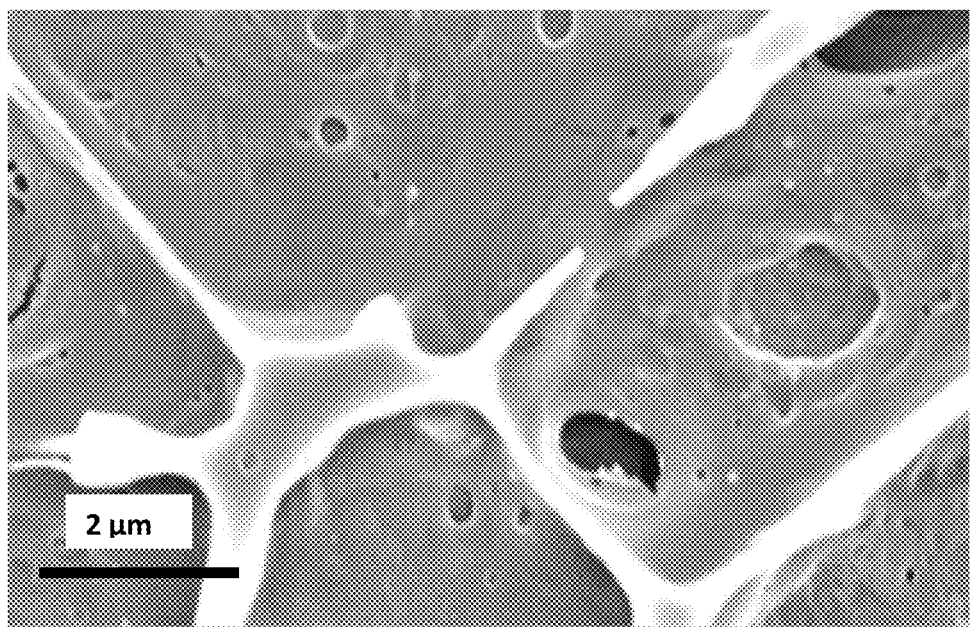
FIG. 18B: shows a SEM image of Composition 18 made in Example 4 for a closer view of its structure.
Figure 19A:
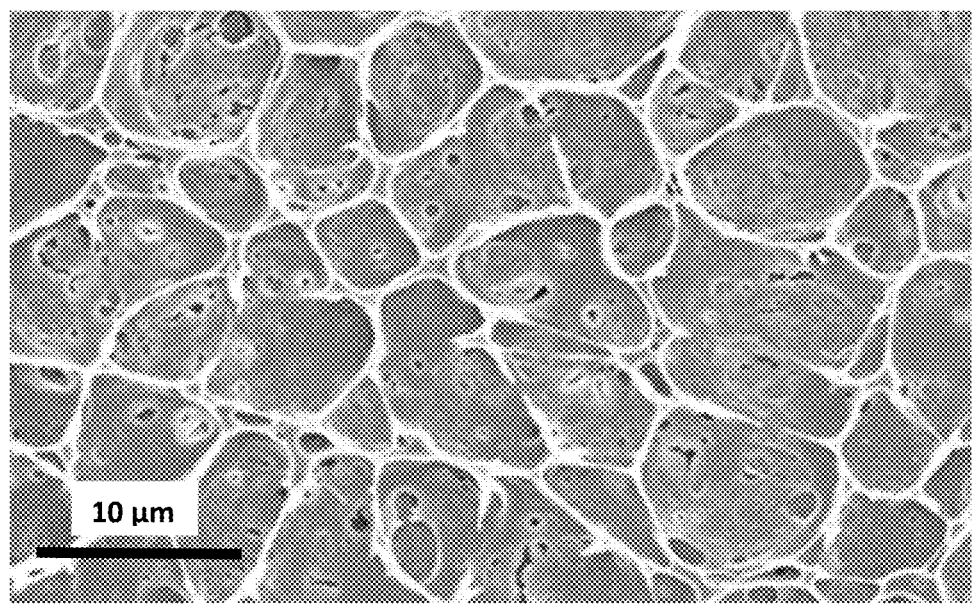
FIG. 19A: shows a SEM image of Composition 19 made in Example 4.
Figure 19B:
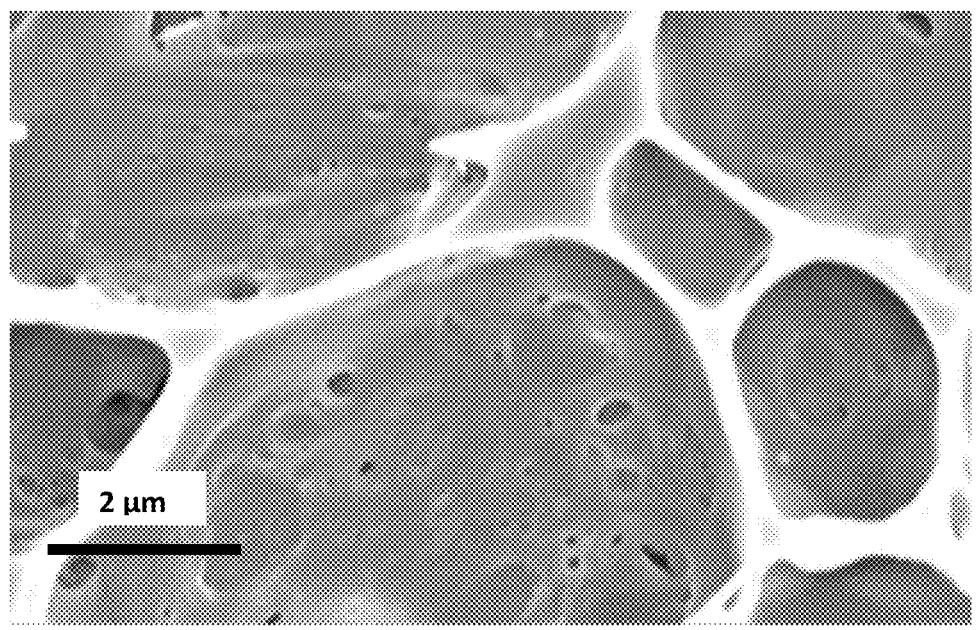
FIG. 19B: shows a SEM image of Composition 19 made in Example 4 for a closer view of its structure.
Figure 20A:
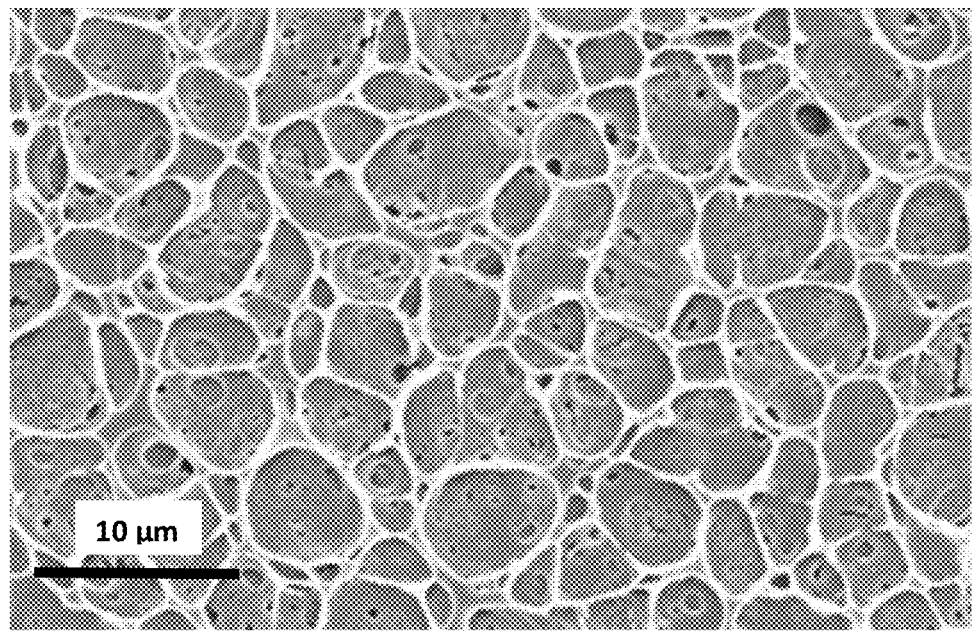
FIG. 20A: shows a SEM image of Composition 20 made in Example 4.
Figure 20B:
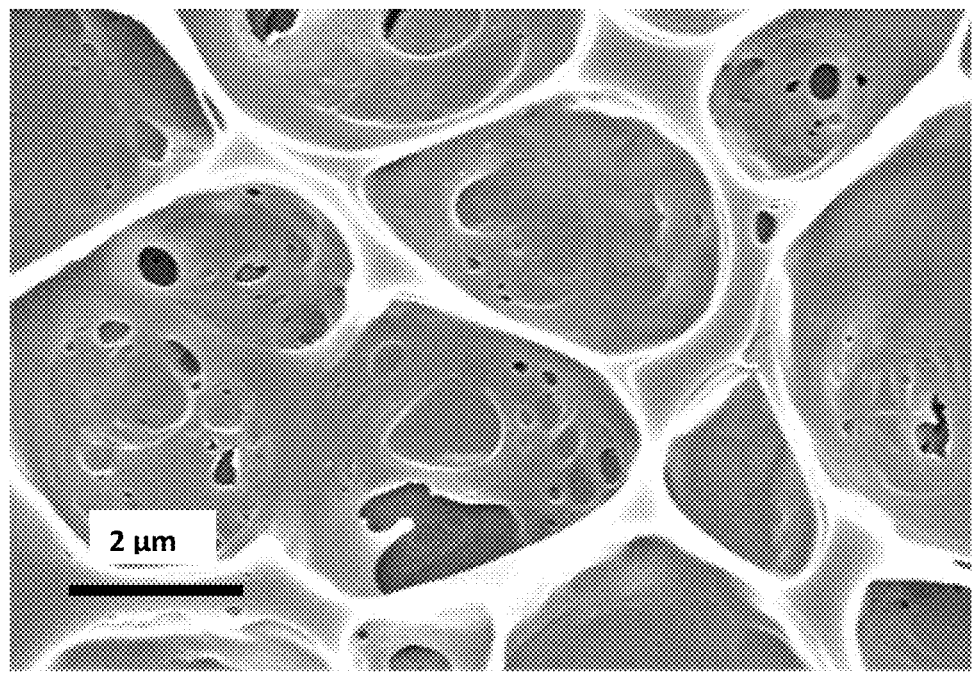
FIG. 20B: shows a SEM image of Composition 20 made in Example 4 for a closer view of its structure.
Figure 21A:
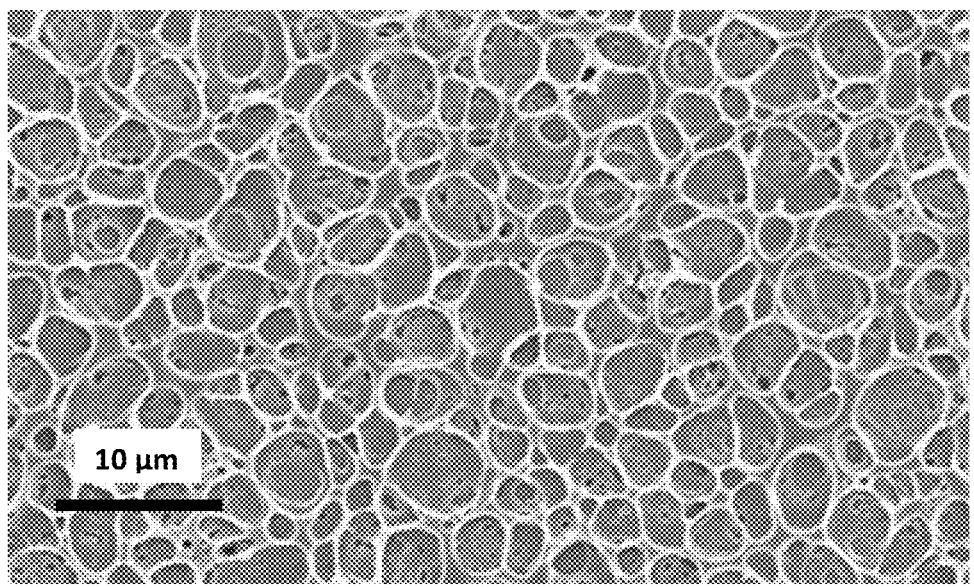
FIG. 21A: shows a SEM image of Composition 21 made in Example 4.
Figure 21B:
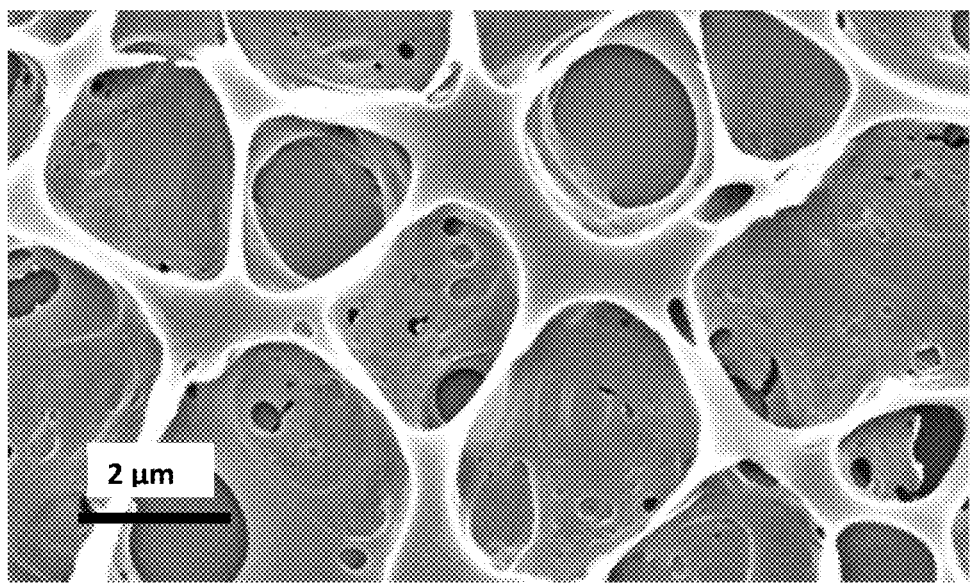
FIG. 21B: shows a SEM image of Composition 21 made in Example 4 for a closer view of its structure.
Figure 22A:
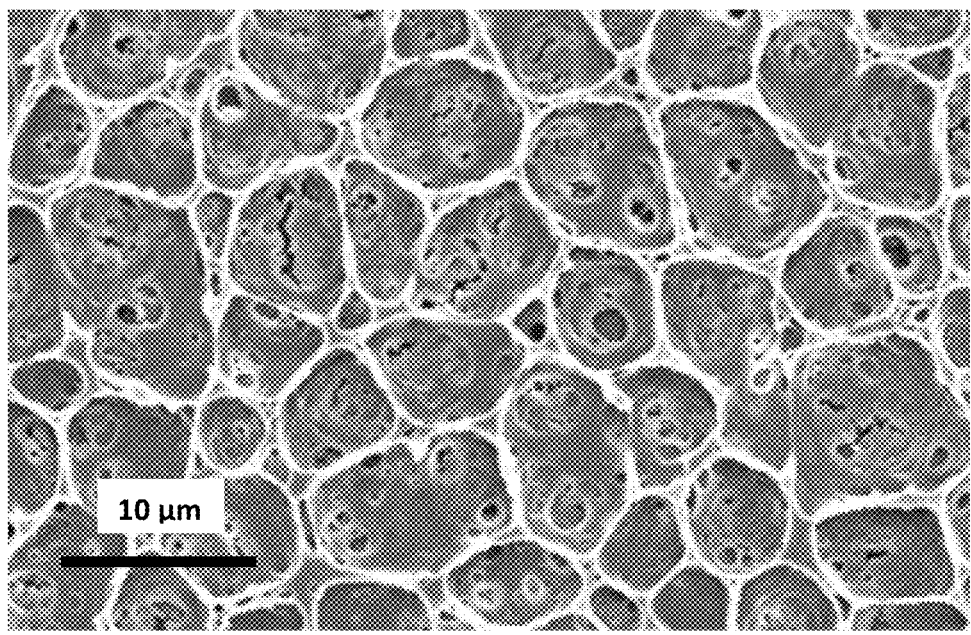
FIG. 22A: shows a SEM image of Composition 22 made in Example 4.
Figure 22B:
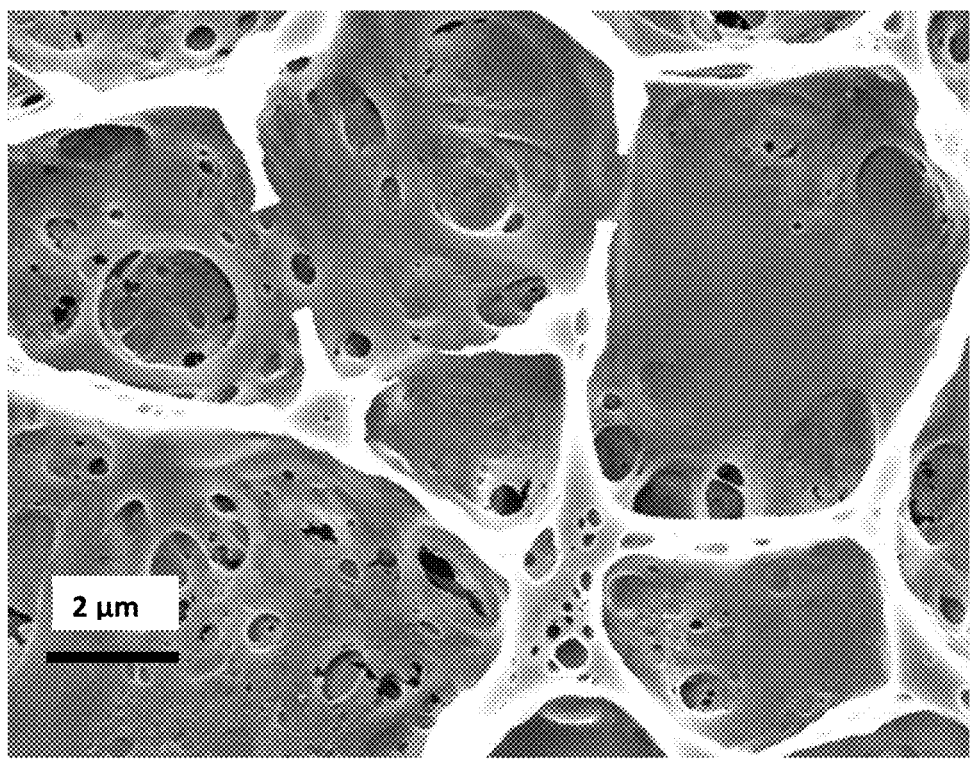
FIG. 22B: shows a SEM image of Composition 22 made in Example 4 for a closer view of its structure.
Figure 23A:
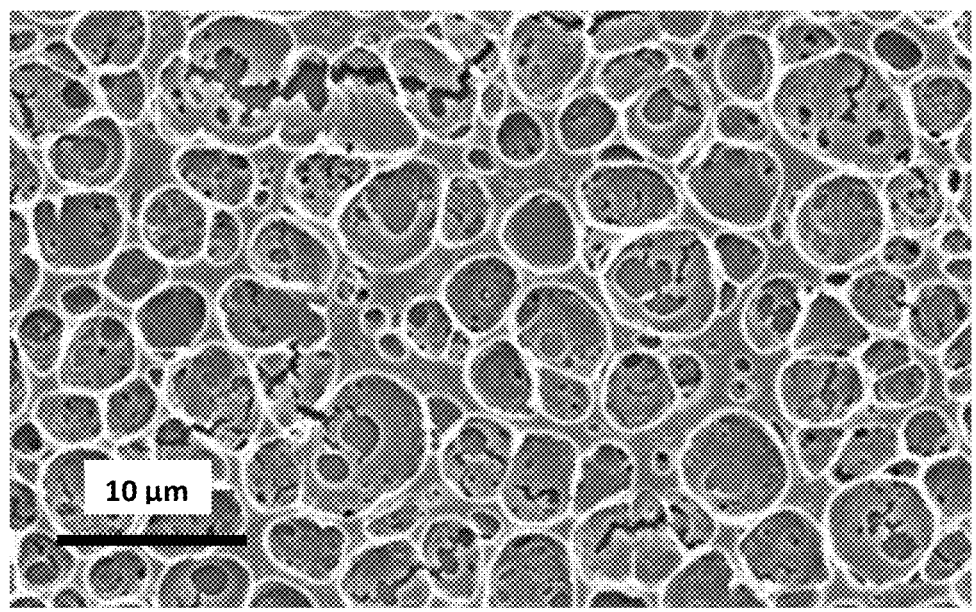
FIG. 23A: shows a SEM image of Composition 23 made in Example 4.
Figure 23B:
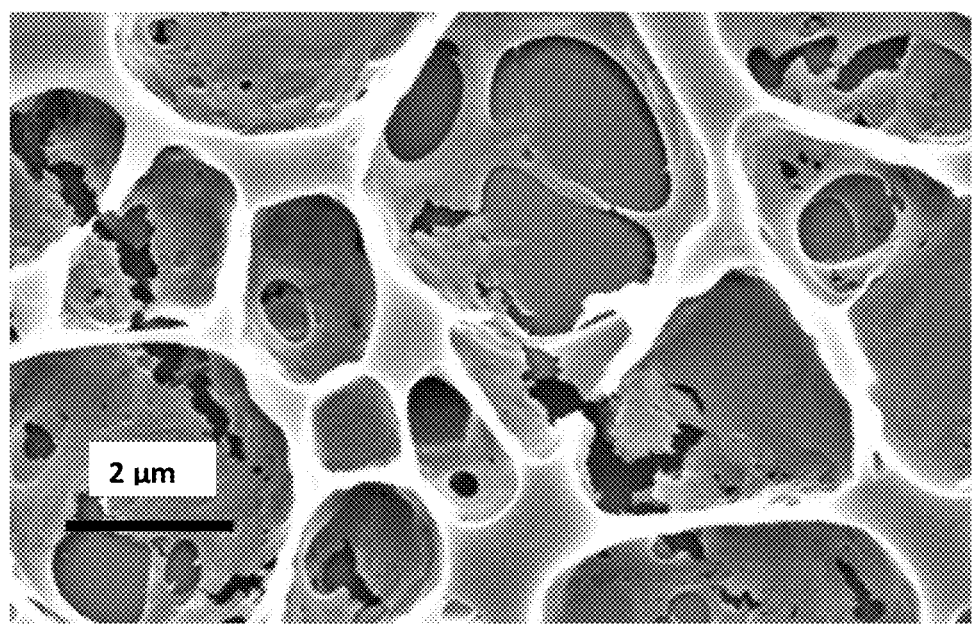
FIG. 23B: shows a SEM image of Composition 23 made in Example 4 for a closer view of its structure.
Figure 24A:
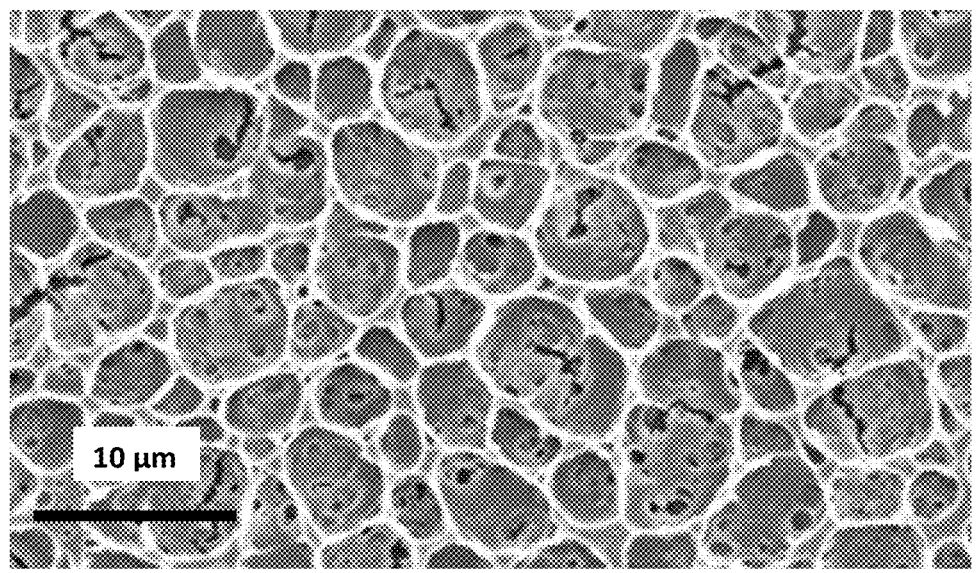
FIG. 24A: shows a SEM image of Composition 24 made in Example 4.
Figure 24B:
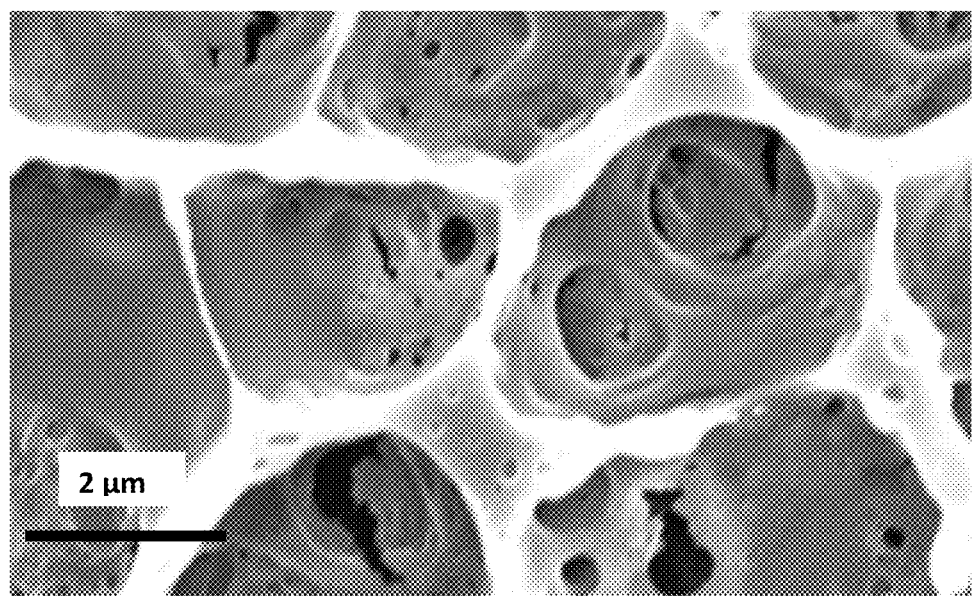
FIG. 24B: shows a SEM image of Composition 24 made in Example 4 for a closer view of its structure.
Figure 25:
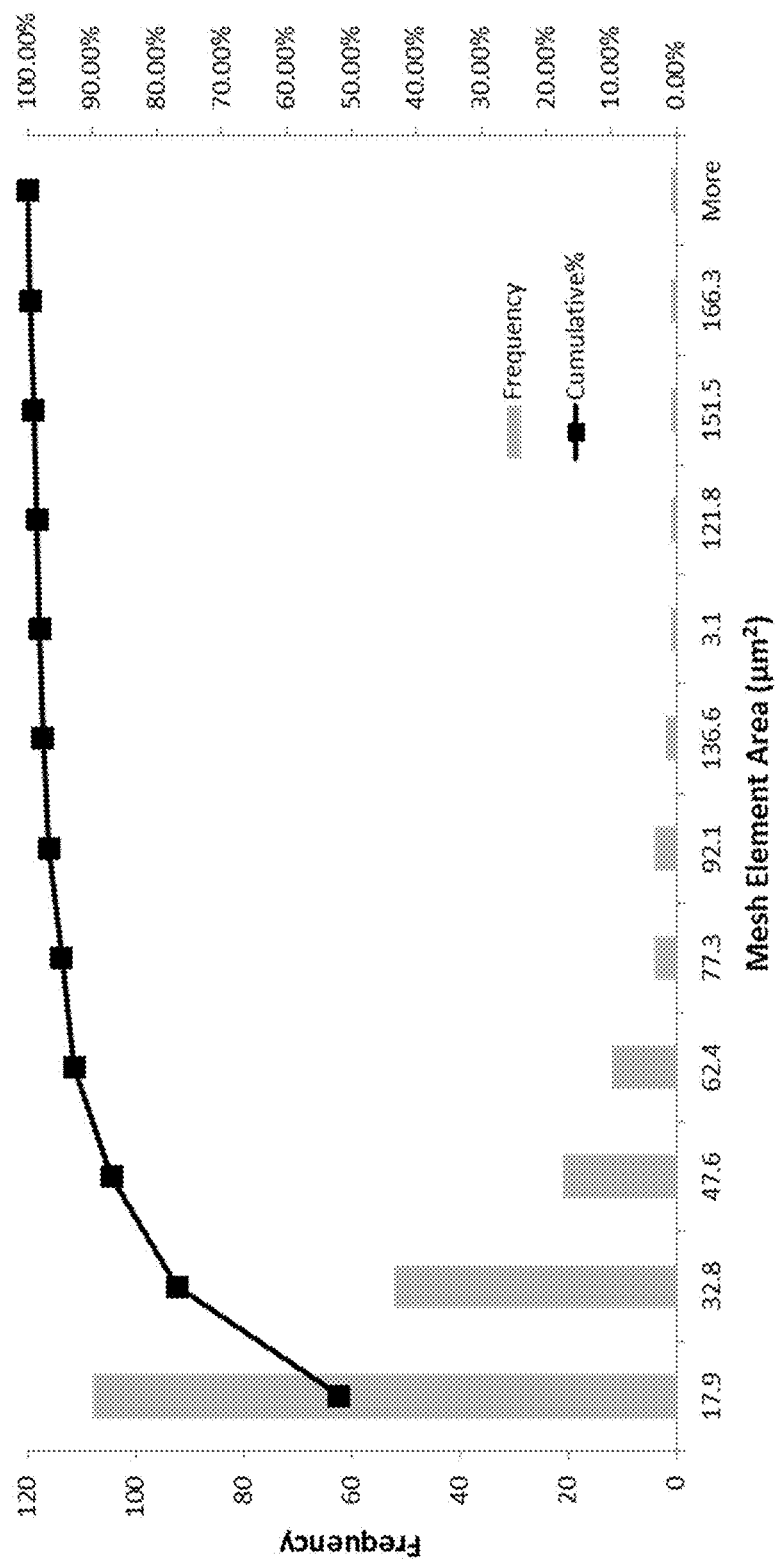
FIG. 25: shows a mesh size distribution graph of Composition 18 made in Example 4.
Figure 26:
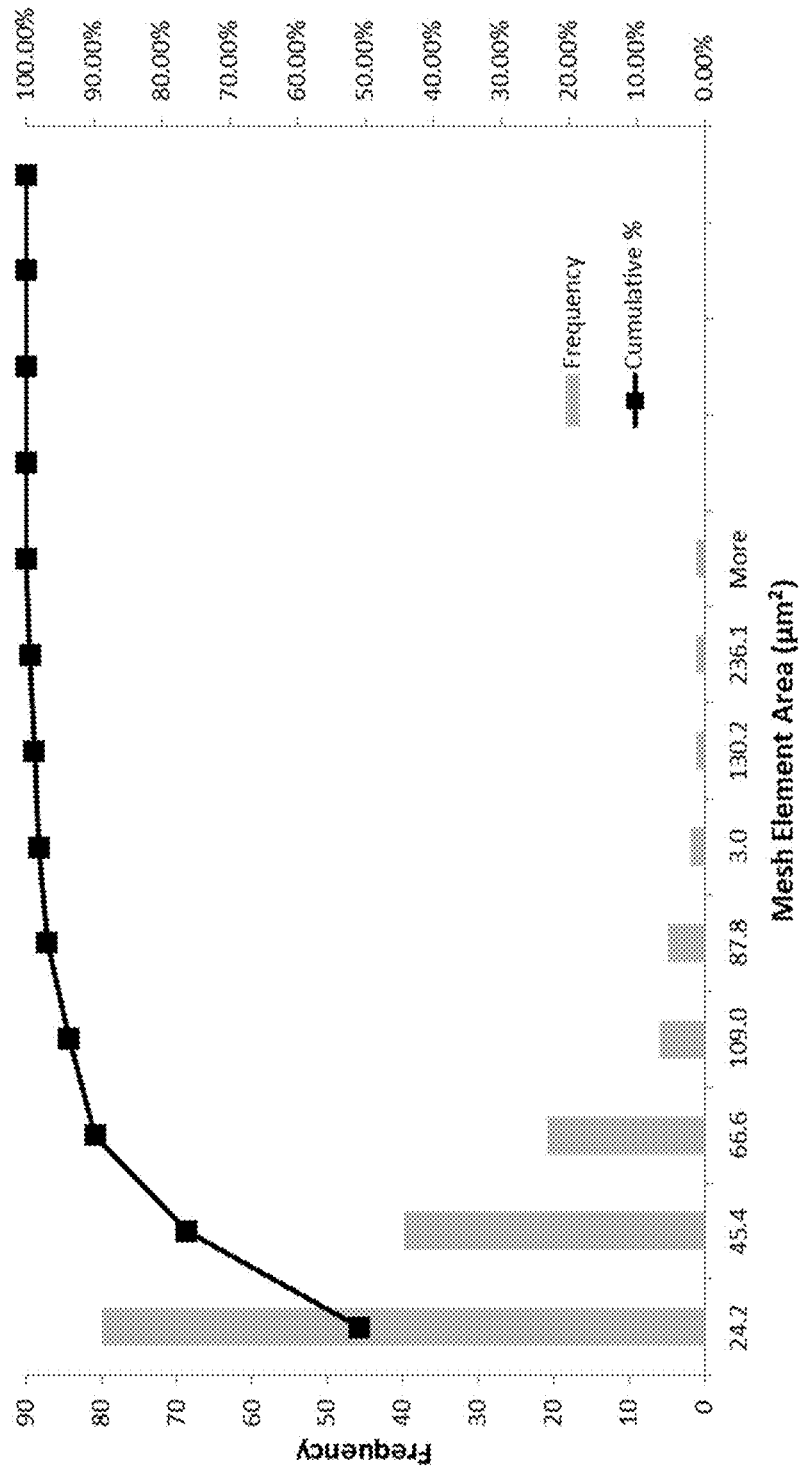
FIG. 26: shows a mesh size distribution graph of Composition 19 made in Example 4.
Figure 27:
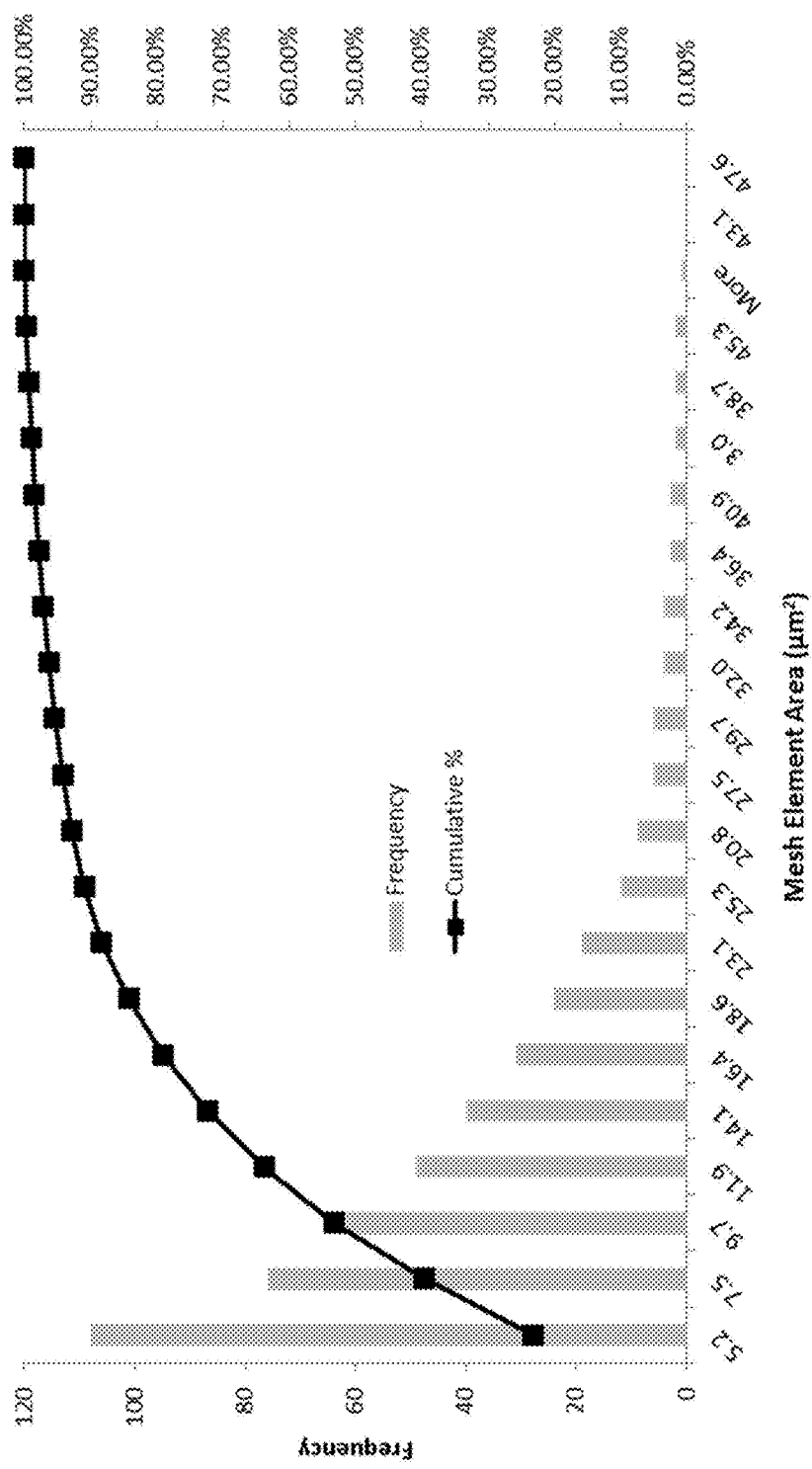
FIG. 27: shows a mesh size distribution graph of Composition 20 made in Example 4.
Figure 28:
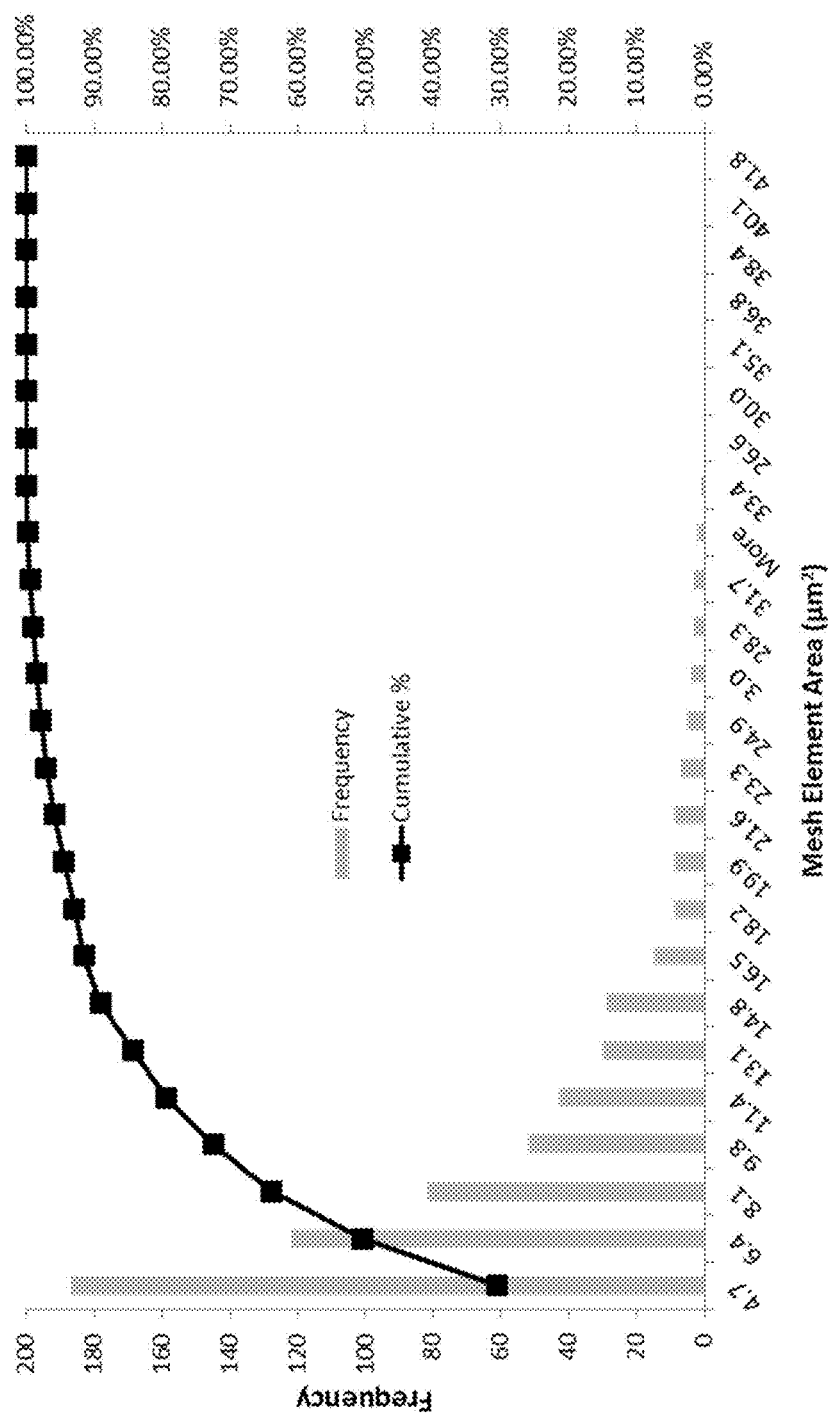
FIG. 28: shows a mesh size distribution graph of Composition 21 made in Example 4.
Figure 29:
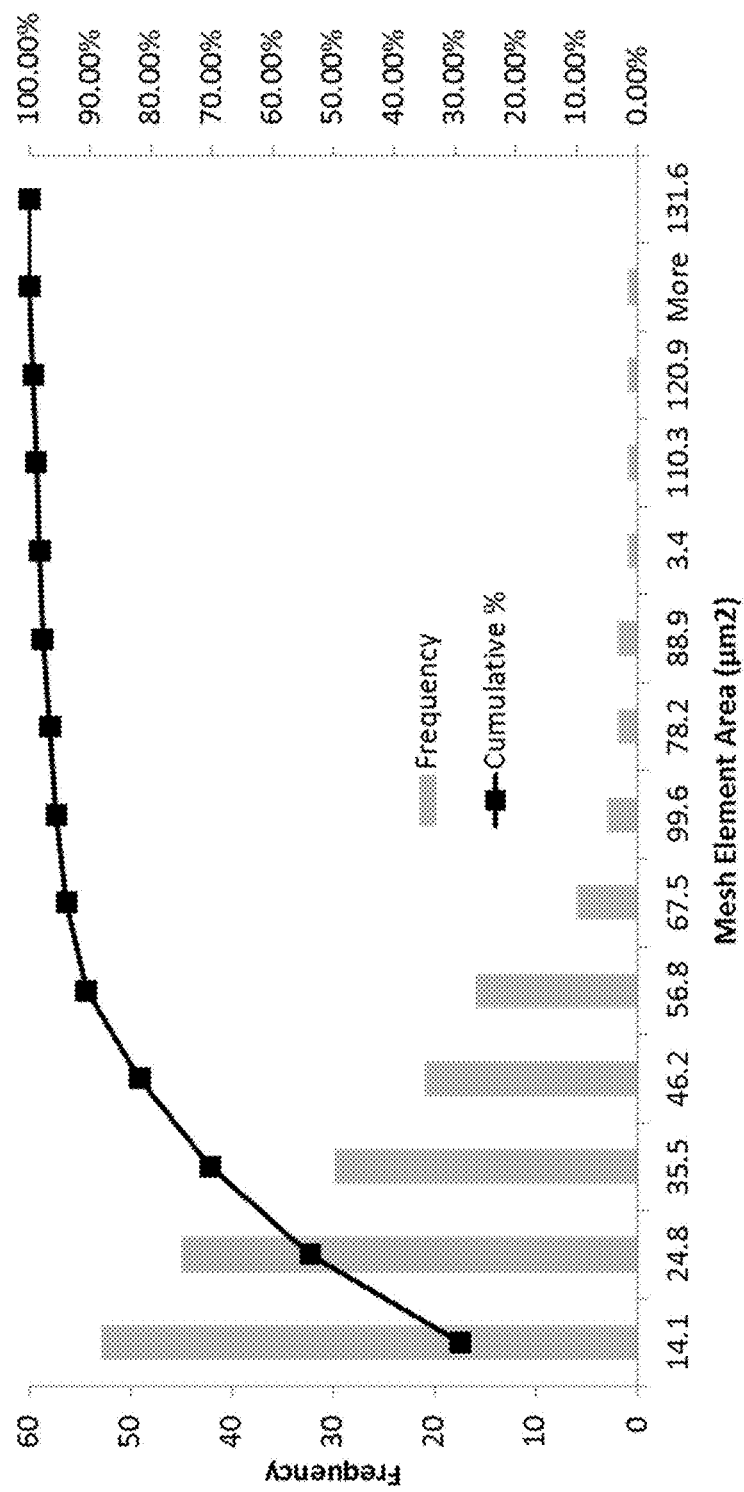
FIG. 29: shows a mesh size distribution graph of Composition 22 made in Example 4.
Figure 30:
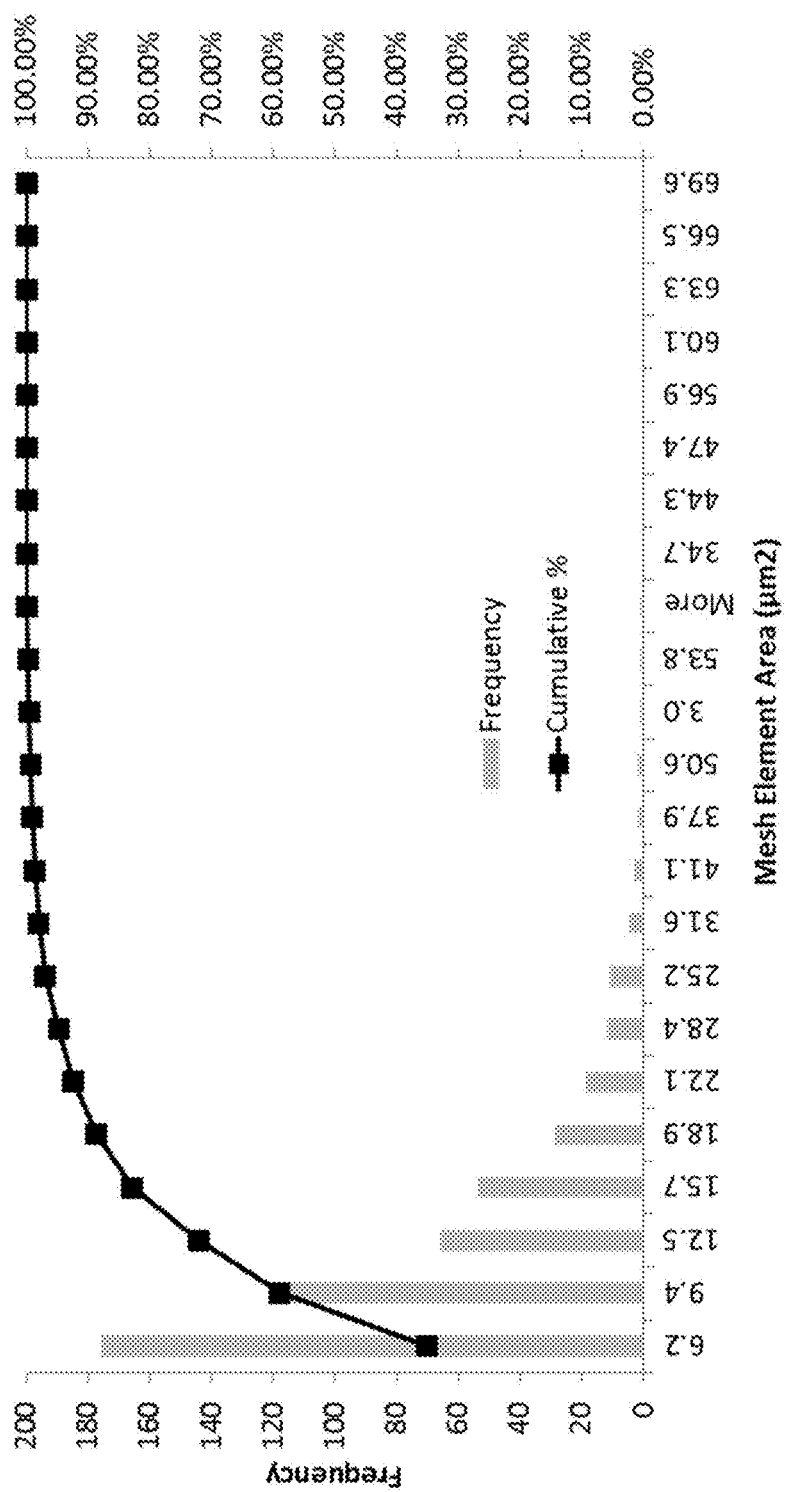
FIG. 30: shows a mesh size distribution graph of Composition 23 made in Example 4.
Figure 31:
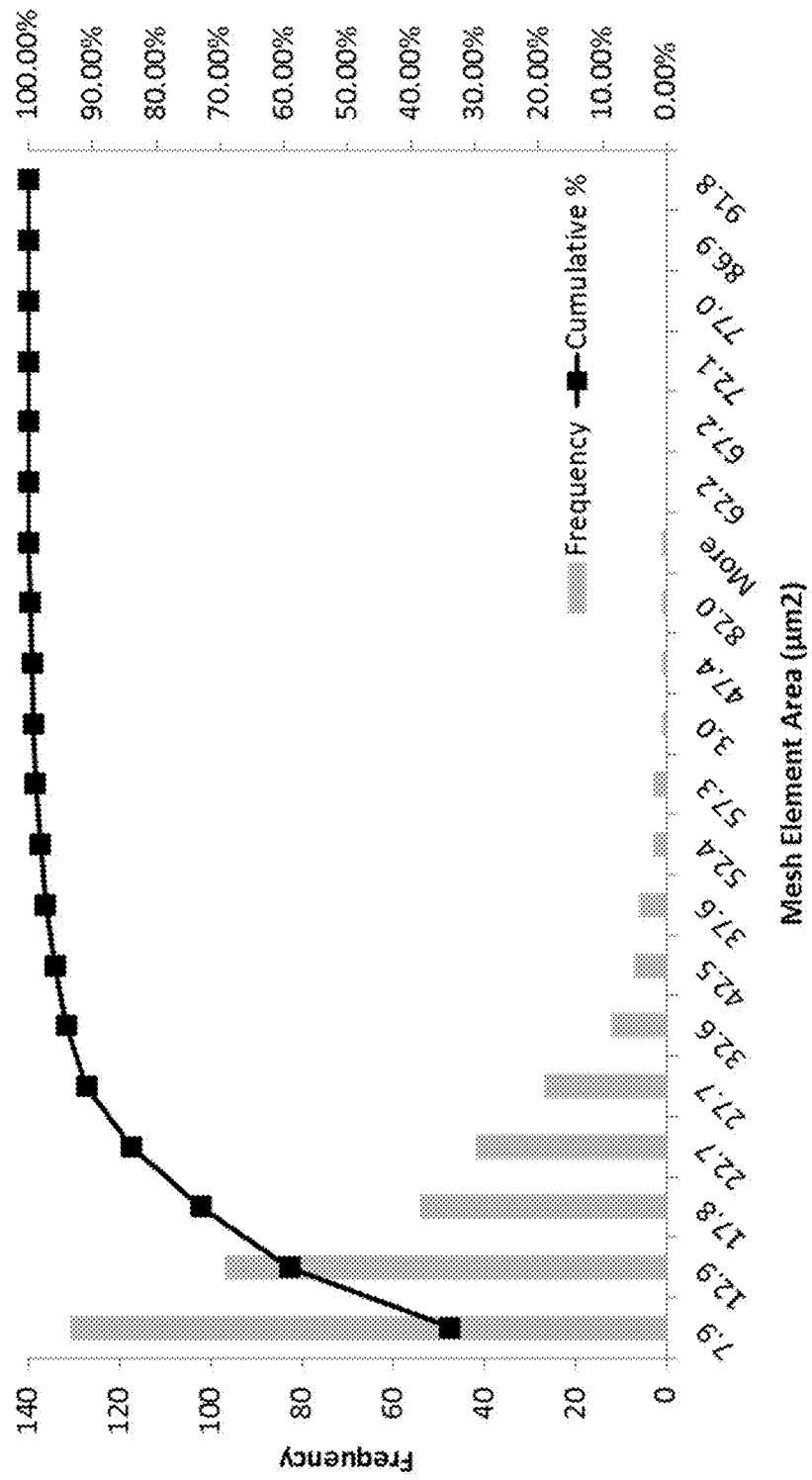
FIG. 31: shows a mesh size distribution graph of Composition 24 made in Example 4.

The composition was scanned with a Zeiss SEM. The SEM images of FIG. 1A and FIG. 1B were in two different scales for a better view of the micro-mesh structure with the scale bars shown the the bottom left corner of each image.

Example 2

Topical compositions were prepared as follows:

| Composition # | Polymer | |
|---|---|---|
| | Trade Name | INCI Name |
| 1 | Sepimax Zen | Polyacrylate Crosspolymer-6 |
| 2 | X-26-7003-1 | Sodium Polyacrylate Crosspolymer-1 |
| 3 | Y-17552 | Polyacrylate Crosspolymer-7 |
| 4 | SR-2038 | Polyacrylic acid/Partial Sodium Salt |
| 5 | Kimica Algin | Sodium Alginate |
| 6 | Sepinov EMT 10 | Hydroxyethyl Acrylate/Sodium Acryloyldimethyl Taurate Copolymer |
| 7 | Cosmedia SP | Sodium Polyacrylate |
| 8 | DynamX H2O | Polyurethane |
| 9 | Methocel K4M | Hydroxypropyl Methylcellulose |
| 10 | Itaconix DSP | Sodium Polyitaconate |
| 11 | Sevol Polyvinyl Alcohol | Polyvinyl Alcohol |

Hydrogels were made by adding ingredients in the order of water (q.s. 100%), Phenoxyethanol (0.5%), HMW HA (0.11%), LMW HA (0.05%), Polymer (0.1%), and Sodium polyaspartate (0.5%) and mixing well to uniform at each step.

SEM images of composition 1-11 are shown on FIGS. 1A-11A and FIGS. 1B-11B, respectively. The SEM images of compositions 1, 2, 4, and 5 clearly show the micro-mesh structure. The SEM images of composition 3 and 7 show a less uniform micro-mesh when compared to images 1, 2, 4 and 5.

Aesthetic tests were done on selected compositions as follows:

| Composition | Aesthetic | Micro-Mesh |
|---|---|---|
| 1 | Cushion on skin Hydrated afterfeel | Yes |
| 5 | Cushion on skin Hydrated afterfeel | Yes |
| 8 | Thin, no cushion on skin Dry afterfeel | No |
| 11 | Less cushion on skin Sticky during transition | No |

The results show that compositions containing the micro-mesh structures show improved aesthetics when compared to those that do not.

Example 3

Compositions were made as follows:

| Composition | Sepixmax Zen (Polyacrylate Crosspolymer-6) (Wt %) | HMW HA (Wt %) | LMW HA (Wt %) | Aquadew (Sodium Polyaspartate) (Wt %) | Chronolux (Tripeptide-32) (Wt %) |
|---|---|---|---|---|---|
| 12 | 0.1 | 0.11 | 0.05 | 0.5 | |
| 13 | 0.1 | 0.11 | 0.05 | | 0.2 |
| 14 | | 0.11 | 0.05 | 0.5 | |
| 15 | 0.1 | | 0.05 | | |
| 16 | | 0.11 | 0.05 | | |
| 17 | 0.1 | | | 0.5 | |

The hydrogel was prepared by adding Phenoxyethanol into water with mixing. The HMW HA solution (Contipro) was added to the mixture and mixed well till uniform (for composition 12, 13, 14 and 16). Then the LMW HA was added to the mixture and mixed well till uniform (for composition 12, 13, 14, 15 and 16). The Polyacrylate crosspolymer-6 was then added and mixed well till uniform (for 12, 13, 15 and 17). The Aquadew SPA-30B (for 12, 14 and 17) or Chronolux (for 13) was added the last and mixed well till uniform.

As shown on FIGS. 12-17, the SEM images of the preferred composition 12 clearly shows the Micro-Mesh structure, while the SEM images of 13, 14 (weak membrane), 15, 16 (weak membrane), 17 do not show the Micro-Mesh structure.

Example 4

Micro-Mesh hydrogels were made as following:

| Composition | Sepixmax Zen (Polyacrylate Crosspolymer-6) (Wt %) | HMW HA (Wt %) | LMW HA (Wt %) | Aquadew (Sodium Polyaspartate) (Wt %) |
|---|---|---|---|---|
| 18 | 0.1 | 0.15 | 0.01 | 0.5 |
| 19 | 0.1 | 0.14 | 0.02 | 0.5 |
| 20 | 0.1 | 0.11 | 0.05 | 0.5 |
| 21 | 0.1 | 0.08 | 0.08 | 0.5 |
| 22 | 0.1 | 0.05 | 0.11 | 0.5 |
| 23 | 0.1 | 0.02 | 0.14 | 0.5 |
| 24 | 0.1 | 0.01 | 0.15 | 0.5 |

The Micro-Mesh hydrogel was prepared by adding Phenoxetol into water with mixing. The HMW Hyaluronic Acid solution was added to the mixture and mixed well till uniform. Then the LMW Hyaluronic Acid was added to the mixture and mixed well till uniform. The Sepimax Zen was then added and mixed well till uniform. The Aquadew SPA-30B was added the last and mixed well till uniform.

SEM images are shown on FIGS. 18A-24A and FIGS. 18B-24B, respectively. All images clearly show the Micro-Mesh structure.

The Micro-Mesh size of each composition was measured. And the Mesh distribution graphs of composition 18-24 are shown on FIGS. 25-31, respectively.

Example 5

Skincare compositions were made as following:

| Ingredient | | Concentration (Wt %) | |
|---|---|---|---|
| Trade Name | INCI Name | 25 | 26 |
| Sepixmax Zen | Polyacrylate Crosspolymer-6 | 0 | 0.1 |
| Hyaluronic Acid, Sodium Salt | Sodium Hyaluronate | 0 | 0.11 |
| Hyactive 10 | Sodium Hyaluronate | 0 | 0.05 |
| Aquadew SPA-30B | Sodium Polyaspartate | 0.5 | 0.5 |
| Purified Water | Water | 36.4 | 36.1 |
| Bifidus Extract Cl Pk Ehg | Water\Aqua\Eau/Bifida Ferment Lysate/ Ethylhexylglycerin | 9.4 | 9.4 |
| Bentone Gel Ihd V | Isohexadecane/Disteardimonium Hectorite/Propylene Carbonate | 7.5 | 7.5 |
| Xiameter Pmx-200 Silicone Fl. 5cs | Dimethicone | 7 | 7 |
| Net Ws-Cf | Dimethicone/Peg-10 Dimethicone/ Disteardimonium Hectorite | 6.25 | 6.25 |
| Glycerine Usp 99% (Vegetable) | Glycerin | 6 | 6 |
| Gransil Dm5 | Dimethicone/Polysilicone-11 | 5 | 5 |
| 1,3 Butylene Glycol | Butylene Glycol | 3 | 3 |
| Bifisomes Pk Ehg | Water\Aqua\Eau/Bifida Ferment Lysate/ Hydrogenated Lecithin | 3 | 3 |
| Dow Corning 2501 Cosmetic Wax | Bis-Peg-18 Methyl Ether Dimethyl Silane | 3 | 3 |
| Hydrovance Moisturizing Agent | Hydroxyethyl Urea | 2 | 2 |
| Sp Arlamol Ps15e-Mbal-Lq-(Ap) | Ppg-15 Stearyl Ether | 1 | 1 |
| Wickenol 131 | Isopropyl Isostearate | 1 | 1 |
| Sucrose, Ultra Pure | Sucrose | 1 | 1 |
| Phytofix | Propylene Glycol Dicaprate/*Helianthus Annus* (Sunflower) Seed Cake/*Hordeum Vulgare* (Barley) Extract/*Cucumis Sativus* (Cucumber) Fruit Extract | 1 | 1 |
| Tixogel Idp 1388 | Isododecane/Polyethylene | 1 | 1 |
| Trehalose Kama | Trehalose | 1 | 1 |
| Hydrolite 5, 2/016020 | Pentylene Glycol | 1 | 1 |
| Polysea Pf | Algae Extract | 0.75 | 0.75 |
| Phenoxetol | Phenoxyethanol | 0.6 | 0.6 |
| Biphyderm Jk | Glycine Soya (Soybean) Extract/Bifida Ferment Lysate | 0.5 | 0.5 |
| Silicone Hl88 | Dimethicone | 0.5 | 0.5 |
| Vitamin E, Usp, Fcc, Code 0420085 | Tocopheryl Acetate | 0.5 | 0.5 |
| Caffeine Powder | Caffeine | 0.2 | 0.2 |
| Chronolux | Water\Aqua\Eau/Butylene Glycol/ Tripeptide-32 | 0.2 | 0.2 |
| Sorbitol Solution 70% | Sorbitol | 0.1 | 0.1 |
| Catacell | Yeast Extract | 0.1 | 0.1 |
| Camelina Oil | Camelina Sativa Seed Oil | 0.1 | 0.1 |
| BHT | BHT | 0.09 | 0.09 |
| Viapure Poria | Poria Cocos Extract | 0.05 | 0.05 |
| Tristat Sdha | Sodium Dehydroacetate | 0.05 | 0.05 |
| EDETA Bd/Na2 | Disodium EDTA | 0.05 | 0.05 |
| Roxisomes O | Water\Aqua\Eau/Yeast Extract/Lecithin | 0.05 | 0.05 |
| Adasomes | *Lactobacillus* Ferment/Lecithin/ Water\Aqua\Eau | 0.05 | 0.05 |
| Aminopropyl Ascorbyl Phosphate | Aminopropyl Ascorbyl Phosphate | 0.045 | 0.045 |
| Chamomile Romaine Oil 627 | Anthemis Nobilis (Chamomile) | 0.015 | 0.015 |
| Silymarin | Lady's Thistle (*Silybum Marianum*) Fruit Extract | 0.015 | 0.015 |
| A00138 Phytoclar Ii Bg Nextgen | Butylene Glycol/*Scutellaria Baicalensis* Root Extract/ *Morus* Bombycis Root Extract | 0.01 | 0.01 |

-continued

| Ingredient | | Concentration (Wt %) | |
|---|---|---|---|
| Trade Name | INCI Name | 25 | 26 |
| Phytosphingosine | Phytosphingosine | 0.01 | 0.01 |
| Mangosteen 90% (324880) | *Garcinia Mangostana* Peel Extract | 0.01 | 0.01 |
| Phyko-Ai Pf | Water/Hydrolyzed Algin | 0.005 | 0.005 |
| White Birch Extract Premier | *Betula Alba* (Birch) Extract | 0.001 | 0.001 |
| Pure Oxy Red 1x-34-Pc-3551 | Iron Oxides | 0.0005 | 0.0005 |

Composition 25 and 26 were made from almost the same ingredients other than that composition 25 does not have the polymer (Sepimax Zen), HMW HA and LMW HA. It was shown in Example 3 that these three ingredients are essential to form the Micro-Mesh structure. Therefore, composition 25 was considered without Micro-Mesh and composition 26 was considered with Micro-Mesh.

A clinical study was performed on fifteen panelists to evaluate the compact of compositions 25 and 26 on the thickness of the stratum corneum of the under-eye area. The test areas in this study were the left and the right under-eye area. A split face study was performed where 300 μL of the compositions 25 and 26 was applied on the left and right side of the face. Compositions were applied in a left/right randomized way. The stratum corneum was evaluated in the under-eye area at baseline and 4 hours after treatment by Reflectance Confocal Microscopy (RCM). A handheld Vivascope 3000 (Lucid, 1.5×, field of view=0.5×0.5 mm) was used in which the contrast is provided by differences in refractive index (SOP A.18v1, labbook 1846-1 p99). At least 5 Vivastacks with a minimal optical slice thickness of 1.96 μm were recorded of the different test areas. Aquasonic clear gel was used as immersion fluid between the objective lens and the tissue cap as well as between the tissue cap and the skin. The thickness of the stratum corneum was determined by measuring the difference in depth between the top of the stratum corneum and the top of the stratum granulosum (first layer with visible cells). Data on the different compositions were collected on the same panelist and statistically evaluated with a paired Student's t-test. Differences over time and between treatments were considered as significant if $p \leq 0.05$.

The stratum corneum was evaluated with Reflectance Confocal Microscopy (RCM) using the Vivascope 3000. Confocal images were used to determine the thickness of the stratum corneum at baseline and 4 hours after treatment.

Figure 32:
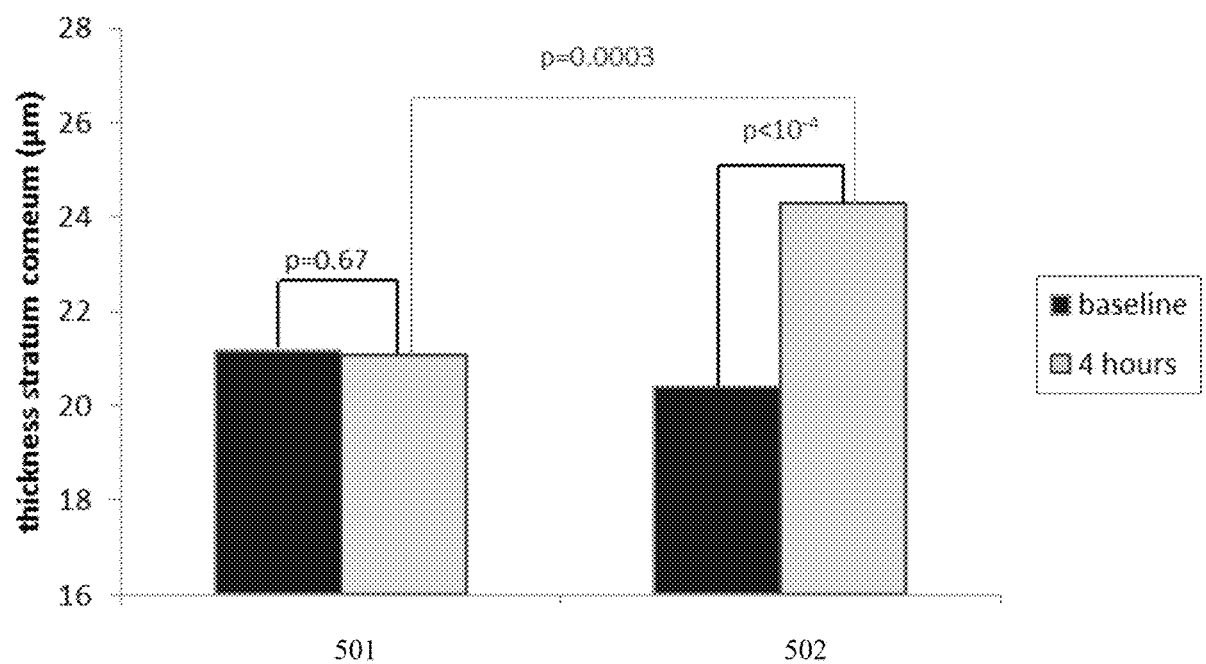
FIG. 32: shows effect of composition 25 and 26 on the thickness of the stratum corneum in the under-eye area.

Four hours after treatment with the composition 26, the stratum corneum thickness increased significantly in the under-eye area compared to baseline ($p<10^{-4}$) (see FIG. 32). There was a significant difference in stratum corneum thickness between the side treated with composition 25 and 26 ($p=0.0003$). For composition 25 no difference was found compared to baseline ($p=0.67$).

Figure 33:
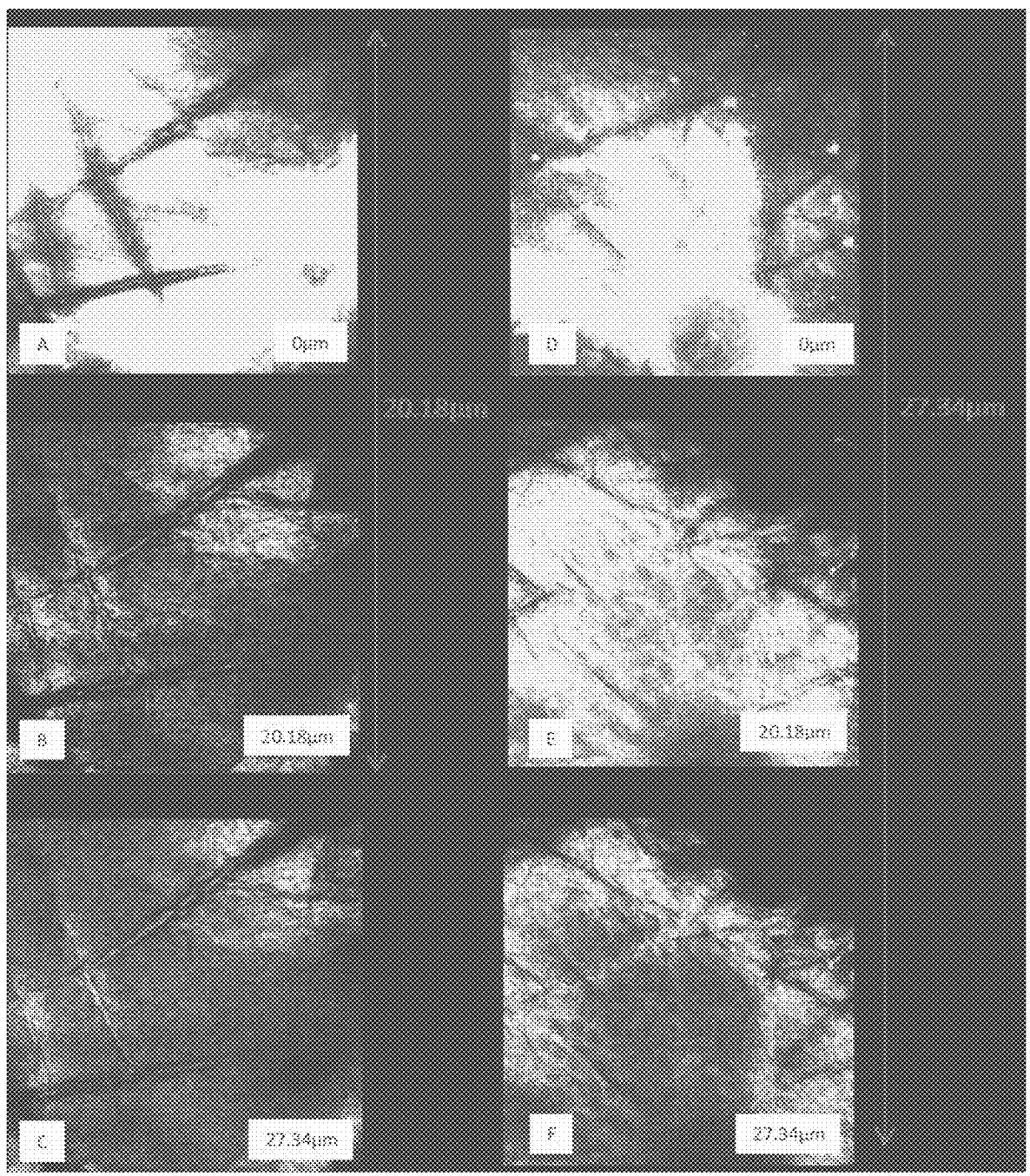
FIG. 33: shows images recorded of the stratum corneum (A, D, E) and the stratum granulosum (B, C, F) of the under-eye area 4 hours after the application of composition 25 (A, B, C) and the composition 26 (D, E, F). Field of view: 0.5 mm×0.5 mm.

FIG. 33 shows representative reflectance confocal images of the stratum corneum and the stratum granulosum of the under-eye area of one panelist taken 4 hours after product application. On each image the depth of recording (average of 5 'stacks') is given. On the site treated with the composition 25 (image A, B, C), the stratum granulosum (image B) was detected at 20.18 μm below the top of the stratum corneum (image A). At the site treated with composition 25 (image D, E, F) the stratum granulosum (image F) was detected at 27.34 μm below the top of the stratum corneum (image D). This illustrates the thickening of the stratum corneum on the composition 26 treated site.

Based on non-invasive images, taken by Reflectance Confocal Microscopy, the thickness of the stratum corneum under the eye was evaluated at baseline and 4 hours after treatment with a formulation with and without Micro-Mesh technology. A significant increase in thickness of the stratum corneum was shown 4 hours after treatment with the 'Micro-Mesh' composition (26). The formulation without 'Micro-Mesh' technology (25) did not have such an effect and the stratum corneum thickness was significantly thicker on the 'Micro-Mesh' treated site compared to the site treated without the 'micro mesh' technology. This illustrates an instant physical plumping effect of the stratum corneum of the under-eye area by the Micro-Mesh technology.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

The invention claimed is:

1. A method for formulating a topical composition containing a micro-mesh comprising the steps of:

a) making a plurality of combinations of a test polymer, at least one LMW HA, at least one HMW HA, a polyamino acid and/or its salt, and water;

wherein the test polymer is selected from the group consisting of an acrylic or methacrylic resin, an acrylate crosslinked silicone copolymer, an anionic polysaccharide; and mixtures thereof;

wherein the polyamino acid and/or its salt is a polymer of aspartic acid and/or its salt having the repeat units:

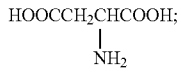

b) using SEM to determine whether a micro-mesh is formed for each of said combinations;

c) repeating the step (a) and (b) with a plurality of said combinations until a micro-mesh is determined to be formed by using SEM;

d) selecting the test polymer that forms a micro-mesh; and e) formulating a topical product that contains the same combination of ingredients that forms the micro-mesh in the same ratios and percentages as are found when the test polymer, LMW HA, HMW HA, polyamino acid, and water alone are combined.

2. The method of claim 1 wherein the polymer is an acrylic or methacrylic resin.

3. The method of claim 1 wherein the polymer is an acrylate crosslinked silicone copolymer.

4. The method of claim 1 wherein the polymer is an anionic polysaccharide.

5. The method of claim 2 wherein the acrylic or methacrylic resin is Sodium Polyacrylate Crosspolymer-1.

6. The method of claim 2 wherein the acrylic or methacrylic resin is Polyacrylic acid/Partial Sodium Salt.

7. The method of claim 3 wherein the acrylate crosslinked silicone copolymer is Polyacrylate Crosspolymer-7.

8. The method of claim 4 wherein the anionic polysaccharide is sodium alginate.

9. The method of claim 1 wherein the HMW HA has a molecular weight ranging from $1\times10^6$ Dalton to $8\times10^6$ Daltons.

10. The method of claim 1 wherein the LMW HA has a molecular weight ranging from $1\times10^3$ Dalton to $8\times10^5$ Daltons.

11. The method of claim 1 wherein the polyamino acid and/or its salt is present in an amount ranging from 0.001 to 10% by weight of the total composition.

12. The method of claim 11 wherein the polyamino acid and/or its salt is present in the form of a salt.

13. The method of claim 12 wherein the polyamino acid salt and/or its salt is a polymer of aspartic acid, sodium salt

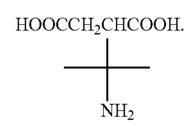

14. The method of claim 13 wherein the polymer of aspartic acid, sodium salt is sodium polyaspartate having a molecular weight ranging from 2,000 to 6,000 Daltons.

* * * * *